(12) United States Patent
Li et al.

(10) Patent No.: US 12,343,096 B2
(45) Date of Patent: Jul. 1, 2025

(54) SURGICAL INSTRUMENT AND OPERATION ROBOT

(71) Applicant: CHENGDU BORNS MEDICAL ROBOTICS INC., Sichuan (CN)

(72) Inventors: Yao Li, Sichuan (CN); Yuan Yuan, Sichuan (CN); Junjie Gong, Sichuan (CN); Tong Liu, Sichuan (CN); Jianping Chen, Sichuan (CN); Peng Wnag, Sichuan (CN)

(73) Assignee: CHENGDU BORNS MEDICAL ROBOTICS INC., Chengdu (CN)

( * ) Notice: Subject to any disclaimer, the term of this patent is extended or adjusted under 35 U.S.C. 154(b) by 995 days.

(21) Appl. No.: 17/428,069

(22) PCT Filed: Dec. 17, 2020

(86) PCT No.: PCT/CN2020/137277
§ 371 (c)(1),
(2) Date: Aug. 3, 2021

(87) PCT Pub. No.: WO2021/121331
PCT Pub. Date: Jun. 24, 2021

(65) Prior Publication Data
US 2022/0125528 A1    Apr. 28, 2022

(30) Foreign Application Priority Data

Dec. 17, 2019    (CN) .......................... 201911303313.3
Dec. 17, 2019    (CN) .......................... 201911303337.9
(Continued)

(51) Int. Cl.
*A61B 34/30*    (2016.01)
*A61B 17/00*    (2006.01)
(Continued)

(52) U.S. Cl.
CPC .... *A61B 34/30* (2016.02); *A61B 2017/00477* (2013.01); *A61B 2017/2902* (2013.01);
(Continued)

(58) Field of Classification Search
CPC ..... A61B 17/32; A61B 34/30; A61B 2017/29; A61B 17/29; A61B 2034/30;
(Continued)

(56) References Cited

U.S. PATENT DOCUMENTS

| 7,822,466 B2 | 10/2010 | Stoianovici et al. |
| 9,259,282 B2 | 2/2016 | Blohm et al. |

(Continued)

FOREIGN PATENT DOCUMENTS

| CN | 102630154 A | 8/2012 |
| CN | 203752148 U | 8/2014 |

(Continued)

OTHER PUBLICATIONS

International Search Report (Translation) for International Patent Application No. PCT/CN2018/097541; mailed Dec. 18, 2018; 2 pages.

(Continued)

*Primary Examiner* — Katherine H Schwiker
*Assistant Examiner* — Zehra Jaffri

(57) ABSTRACT

A surgical instrument comprising: an execution assembly; a control assembly connected with the execution assembly to control opening, closing, spin and deflection motions of the execution assembly; an instrument seat for mounting a transmission means, the instrument seat having a first coupling; a sterile isolation seat for mounting a sterile isolation membrane, the sterile isolation seat having a second coupling, and the sterile isolation seat being fixedly connected with the instrument seat; and a motor mounting seat for mounting a driving means, the motor mounting seat having (Continued)

a third coupling, and the sterile isolation seat being fixedly connected with the motor mounting seat; wherein the instrument seat is mounted on the sterile isolation seat through a cooperation of the first coupling with the second coupling, the sterile isolation seat being mounted on the motor mounting seat through a cooperation of the second coupling with the third coupling, and the first coupling, the second coupling and the third coupling are coaxially provided.

15 Claims, 14 Drawing Sheets

(30) Foreign Application Priority Data

| Dec. 17, 2019 | (CN) | 201911303341.5 |
|---|---|---|
| Dec. 17, 2019 | (CN) | 201911304691.3 |
| Dec. 17, 2019 | (CN) | 201911304702.8 |
| Dec. 17, 2019 | (CN) | 201911304704.7 |

(51) Int. Cl.
  *A61B 17/29* (2006.01)
  *A61B 17/3201* (2006.01)

(52) U.S. Cl.
  CPC ............... *A61B 2017/2927* (2013.01); *A61B 2017/2932* (2013.01); *A61B 2017/2939* (2013.01); *A61B 2017/2948* (2013.01); *A61B 17/3201* (2013.01)

(58) Field of Classification Search
  CPC .......... A61B 2017/00477; A61B 34/70; A61B 34/71; A61B 2034/715
  See application file for complete search history.

(56) References Cited

U.S. PATENT DOCUMENTS

| 10,993,776 | B2 | 5/2021 | Li |
| 2002/0082612 | A1 | 6/2002 | Moll et al. |
| 2007/0089557 | A1 | 4/2007 | Solomon et al. |
| 2007/0156285 | A1 | 7/2007 | Sillman et al. |
| 2009/0247943 | A1* | 10/2009 | Kirschenman ......... A61B 34/71 604/95.04 |
| 2009/0248039 | A1 | 10/2009 | Cooper et al. |
| 2010/0069920 | A1 | 3/2010 | Naylor et al. |
| 2010/0204713 | A1 | 8/2010 | Ruiz Morales |
| 2010/0225209 | A1 | 9/2010 | Goldberg et al. |
| 2011/0277776 | A1 | 11/2011 | Mcgrogan et al. |
| 2013/0085389 | A1 | 4/2013 | Tsang et al. |
| 2016/0001038 | A1 | 1/2016 | Romo et al. |
| 2017/0079722 | A1 | 3/2017 | O'Grady et al. |
| 2017/0273748 | A1 | 9/2017 | Hourtash et al. |
| 2017/0333141 | A1 | 11/2017 | Itkowitz et al. |
| 2017/0333142 | A1 | 11/2017 | Itkowitz et al. |
| 2018/0168671 | A1* | 6/2018 | Overmyer ............ A61B 34/70 |
| 2018/0168752 | A1* | 6/2018 | Scheib ................. A61B 34/70 |
| 2018/0280095 | A1 | 10/2018 | Lattimore |
| 2019/0038282 | A1* | 2/2019 | Shelton, IV ..... A61B 17/07207 |

FOREIGN PATENT DOCUMENTS

| CN | 105816243 A | 8/2016 |
| CN | 105832488 A | 8/2016 |
| CN | 205790724 U | 12/2016 |
| CN | 107260308 A | 10/2017 |
| CN | 107260311 A | 10/2017 |
| CN | 107374734 A | 11/2017 |
| CN | 206880734 U | 1/2018 |
| CN | 207870965 U | 9/2018 |
| CN | 209564148 U | 11/2019 |
| CN | 209564150 U | 11/2019 |
| CN | 209564154 U | 11/2019 |
| CN | 111012385 A | 4/2020 |
| CN | 111685875 A | 9/2020 |
| CN | 111685876 A | 9/2020 |
| CN | 111685878 A | 9/2020 |
| CN | 111685886 A | 9/2020 |
| CN | 211834690 U | 11/2020 |
| CN | 211834694 U | 11/2020 |
| CN | 212261515 U | 1/2021 |
| CN | 212261518 U | 1/2021 |
| WO | 2017220822 A1 | 12/2017 |
| WO | 2018118922 A1 | 6/2018 |
| WO | 2018119136 A1 | 6/2018 |

OTHER PUBLICATIONS

International Search Report, Written Opinion, and Claims (Translation) for PCT International App. Serial No. PCT/CN2018/097467; mailed Oct. 8, 2018; 9 pages.
Supplementary European Search Report of the European Patent Office, Issued in European Application No. 18915439.6-1113; dated Jan. 4, 2022; 8 pages.
First Office Action of Counterpart Chinese Patent Application No. 201911303337.9 issued on Oct. 1, 2024.
First Office Action of Counterpart Chinese Patent Application No. 201911303313.3 issued on Sep. 19, 2024.
First Office Action of Counterpart Chinese Patent Application No. 201911304704.7 issued on Sep. 27, 2024.
International Search Report of PCT Patent Application No. PCT/CN2020/137277 issued on Mar. 16, 2021.
Written Opinion of PCT Patent Application No. PCT/CN2020/137277 issued on Mar. 16, 2021.
Extended European Search Report of counterpart European Patent Application No. 20901870.4 issued on Jun. 4, 2024.

* cited by examiner

SURGICAL INSTRUMENT AND OPERATION ROBOT

CROSS-REFERENCE TO RELATED APPLICATIONS

This application is a national stage application filed under 35 U.S.C. § 371 of International Patent Application No. PCT/CN2020/137277, filed on Dec. 17, 2020, which is incorporated by reference herein in its entirety for all purposes.

TECHNICAL FIELD

The present invention relates to the technical field of operation robots and relates to a surgical instrument and operation robot including the same.

BACKGROUND

During computer-aided telerobotic surgeries, a surgeon usually manipulates a main controller to control at a location that may be remote from a patient (e.g., through an operating room, in a different room or in a building completely different from that of the patient) a motion of a surgical instrument at a surgical site. The main controller usually includes one or more input devices that are coupled to the surgical instrument with a servo motor, for articulating an instrument at the surgical site. The servo motor is usually a part of an electromechanical device or a surgical manipulator ("slave device") supporting and controlling the surgical instrument that has been directly introduced into an open surgical site or introduced into a body cavity (such as a patient's abdominal cavity) through a trocar sleeve. During the surgery, the surgical manipulator provides mechanical articulations and controls over various surgical instruments (such as a tissue grasper, a needle driver and an electrosurgical cautery probe), and each surgical instrument performs various functions for the surgeon, for example, holding or driving a needle, grasping a blood vessel, or dissecting, cauterizing or coagulating tissue. Computer-aided surgeries manipulated remotely reduce the size and number of incisions required during the surgeries, so as to improve the recovery rate of the patient, and also help reduce trauma and discomfort of the patient.

The surgical instrument is provided on a sliding table through a mounting frame. The mounting frame includes an instrument seat, a sterile isolation seat, and a motor mounting seat. However, there are still many areas that need to be improved in terms of the current surgical instruments.

SUMMARY

The present invention is proposed to solve the deficiencies in the prior art. An object of the present invention is to provide an operation instrument assembly and an operation robot including the same in which an instrument seat, a sterile isolation seat, and a motor mounting seat are easy to be disassembled and assembled; efficiency of mounting the instrument seat, the sterile isolation seat, and the motor seat is improved; power of a driving means can be efficiently and stably delivered to a transmission means; an execution assembly and a control assembly with at least three degrees of freedom are provided, where the execution assembly may be bent or straightened at a wrist joint, and may be opened or closed at knuckles; the execution assembly may achieve a greater spin angle, thereby improving flexibility and accuracy of operation manipulation of the surgical robot that is minimally invasive.

According to one aspect of the present invention, a surgical instrument is provided, and the surgical instrument is characterized by comprising: an execution assembly; a control assembly connected with the execution assembly to control opening, closing, spin and deflection motions of the execution assembly; an instrument seat for mounting a transmission means, the instrument seat being provided with a first coupling; a sterile isolation seat for mounting a sterile isolation membrane, the sterile isolation seat being provided with a second coupling, and the sterile isolation seat being fixedly connected with the instrument seat; a motor mounting seat for mounting a driving means, the motor mounting seat being provided with a third coupling, and the sterile isolation seat being fixedly connected with the motor mounting seat; wherein the instrument seat is mounted on the sterile isolation seat through a cooperation of the first coupling with the second coupling, the sterile isolation seat is mounted on the motor mounting seat through a cooperation of the second coupling with the third coupling, and the first coupling, the second coupling and the third coupling are coaxially provided.

By providing the first coupling, the second coupling and the third coupling coaxially, the power of the driving means mounted on the motor mounting seat may be efficiently and stably delivered to the control assembly driving the operation execution assembly, thereby controlling the motion of the execution assembly.

BRIEF DESCRIPTION OF DRAWINGS

In order to explain the embodiments of the present invention or the technical solutions in the prior art more clearly, the drawings that need to be used in the description of the embodiments or the prior art will be briefly introduced below. Obviously, the drawings in the following description are some embodiments of the present invention, and other drawings may be obtained by an ordinary skilled in the art based on the following drawings without inventive labor, in which.

DETAILED DESCRIPTION

In order to make the object, technical solutions and advantages of the present invention clearer, the implementation methods of the present invention will be explained in detail with reference to the accompanying drawings and embodiments, to fully understood and implemented accordingly the implementation procedure as to how the present invention adopts the technical means to solve the technical problems and bring about the technical effects.

Figure 1:
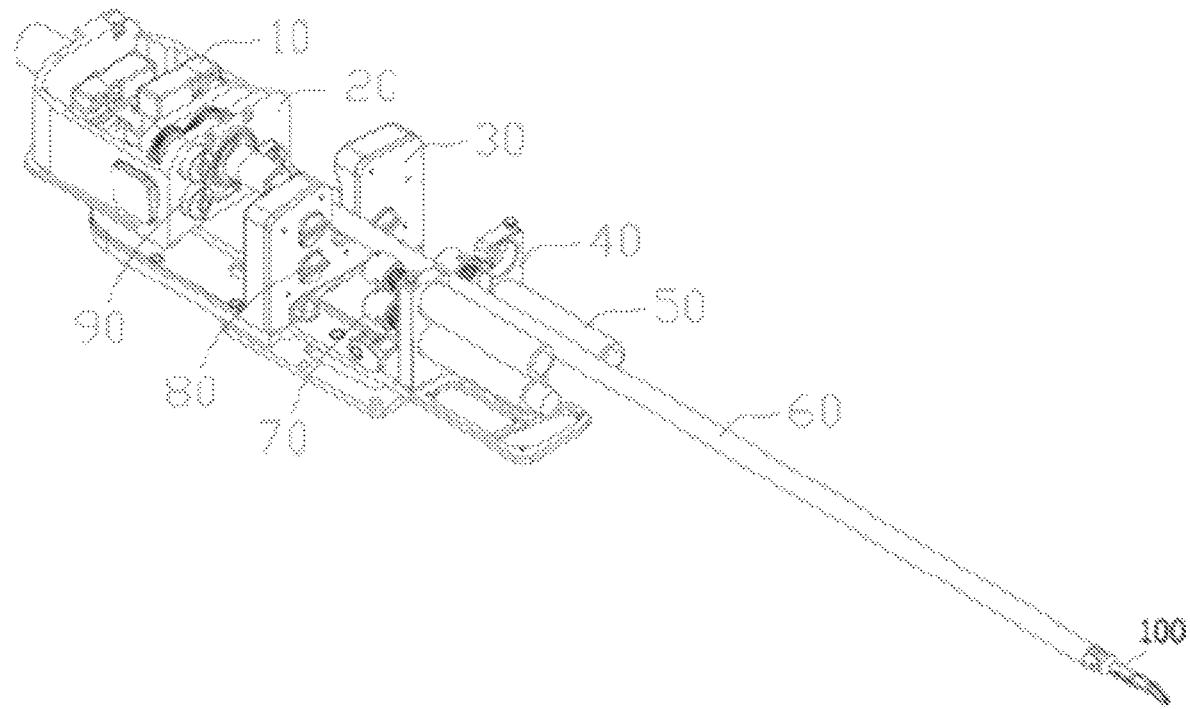
FIG. 1 is a forward structural exploded view of an operation instrument.

The embodiment shown in FIG. 1 provides an operation instrument assembly for an operation robot, including an instrument seat 20, a sterile isolation seat 30, and a motor mounting seat 40. The instrument seat 20 is configured to mount a transmission means 10, the sterile isolation seat 30 is configured to mount a sterile isolation membrane (not shown in the figure), and the motor mounting seat 40 is configured to mount a driving means 50; the driving means 50 here includes but not limited to a motor, and other conventional driving mechanisms are also within the protection scope of the present invention. The transmission means 10 is connected with an operation execution assembly 100 through a control assembly 60, whereby depending on the control of the surgeon, the power from the driving means 50 is delivered to the transmission means 10 of the instrument seat 20, allowing the operation execution assembly 100 to complete more than one degree of freedom.

I. Power Delivering Mechanism

In order to deliver the power from the driving means 50 to the transmission means 10 of the instrument seat 20, a coupling mechanism is provided. As shown in FIG. 1, the instrument seat 20 is provided thereon with at least one first coupling 90, the sterile isolation seat 30 is provided thereon with at least one second coupling 80, and the motor mounting seat 40 is provided thereon with at least one third coupling 70; wherein the instrument seat 20 is mounted on the sterile isolation seat 30 through a cooperation of the first coupling 90 with the second coupling 80, the sterile isolation seat 30 is mounted on the motor mounting seat 40 through a cooperation of the second coupling 80 with the third coupling 70, and the first coupling 90, the second coupling 80 and the third coupling 70 are coaxially provided. The specific mode is as follows: when the instrument seat 20 is mounted on the sterile isolation seat 30, the first coupling 90 is coaxial with the second coupling 80, and when the sterile isolation seat 30 is mounted on the motor mounting base 40, the second coupling 80 is coaxial with the third coupling 70. That is, after the positioning and mounting of the instrument seat 20, the sterile isolation seat 30 and the motor mounting set 40 is completed, the first coupling 90, the second coupling 80 and the third coupling 70 should be coaxial, where the wording "coaxial" here means that the axes thereof coincide.

The operation instrument assembly for the operation robot provided by the embodiment of the present invention greatly improves power transmission effect and ensures stability of the power transmission, by connecting the driving means 50 with the transmission means 10 through three couplings, and providing coaxially the first coupling 90 located on the instrument seat 20, the second coupling 80 located on the sterile isolation seat 30 and the third coupling 70 located on the motor mounting seat 40.

Figure 2:
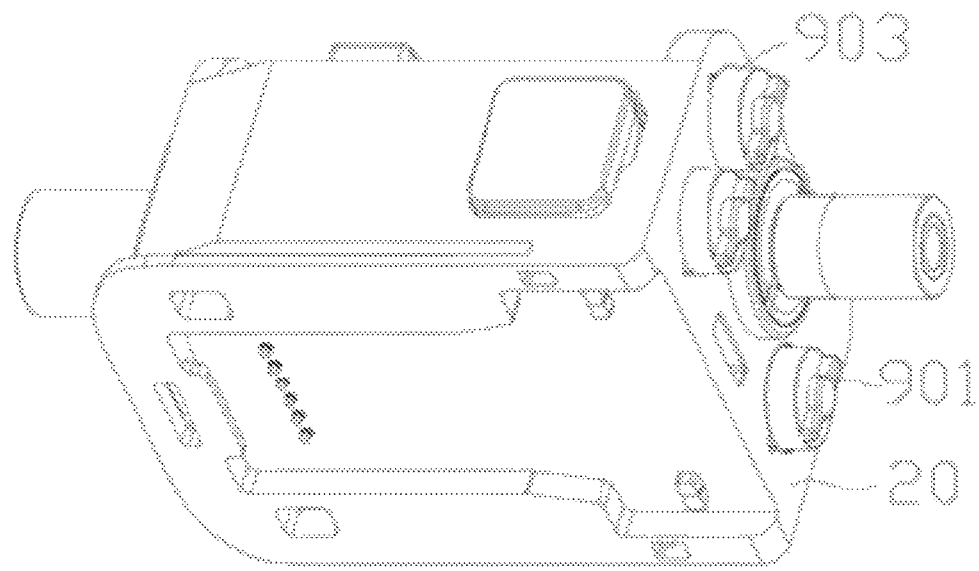
FIG. 2 is a structural schematic view of a first coupling of an operation instrument for an operation robot.

In the embodiment shown in FIG. 2, the first coupling 90 includes a first body 903 and a first protrusion 901. The first body 903 is connected with the transmission means 10; an instrument seat 20 is provided with a first through hole which is rotatably and cooperatively connected with the first body 903, and the first body 903 is rotatably mounted in the first through hole. The first protrusion 901 is provided at an end of the first body 903 close to the sterile isolation seat 30, the first protrusion 901 has edges and corners, that is, the first protrusion 901 is of a non-cylindrical shape, and the specific shape of the first protrusion is preferably straight-shaped, equilateral polygon, etc. The first protrusion is mainly configured to deliver power; therefore, the shape of the first protrusion is within the protection scope of the present invention as long as the first protrusion 901 can prevent the first coupling 90 and the second coupling 80 from rotating relative to each other.

Figure 3:
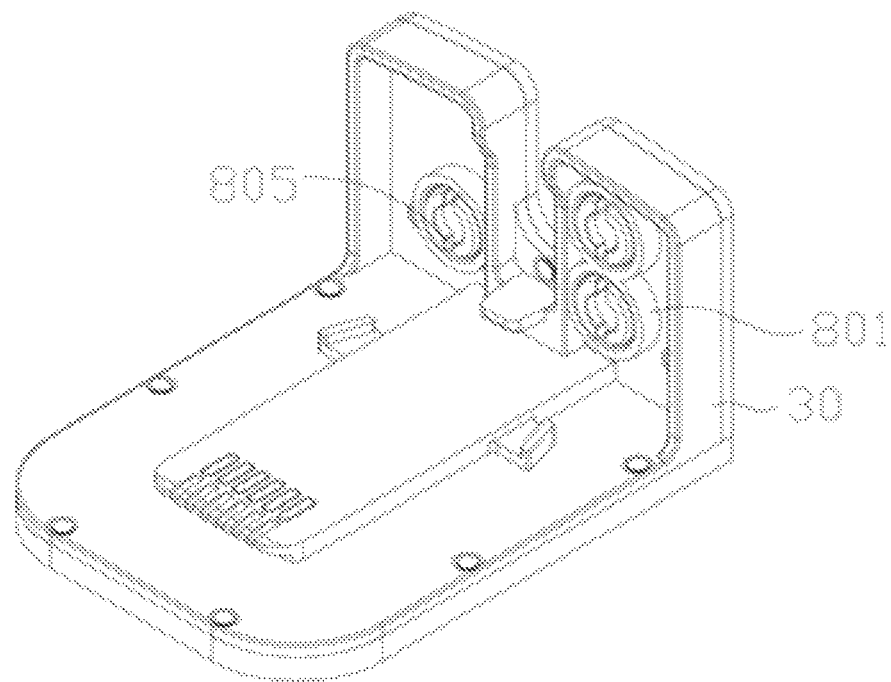
FIG. 3 is a forward structural schematic view of a second coupling of an operation instrument for an operation robot.
Figure 4:
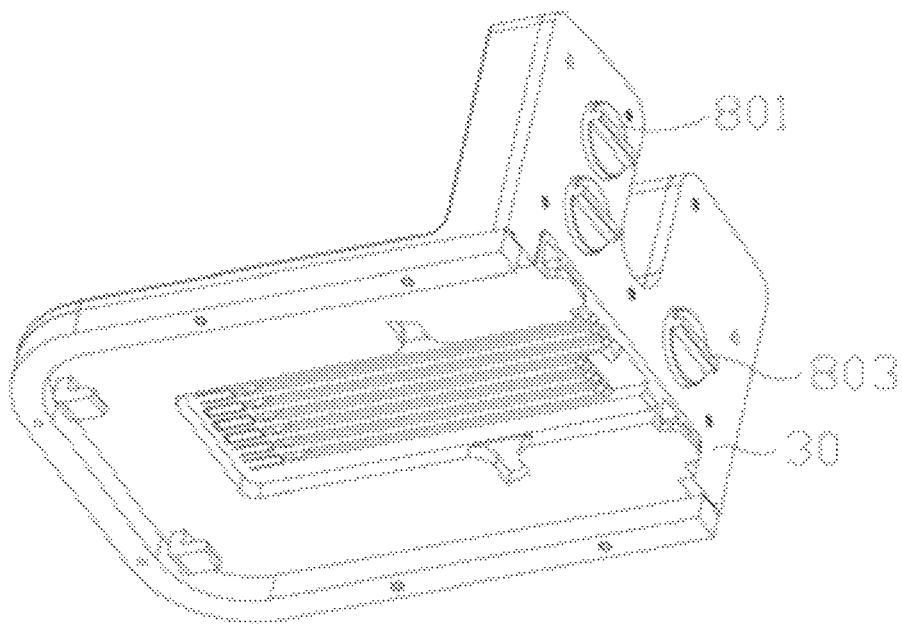
FIG. 4 is a backward structural schematic view of a second coupling of an operation instrument for an operation robot.

In the embodiment shown in FIGS. 3-4, the second coupling 80 includes a second body 801 and a second protrusion 803. The second body 801 is rotatably provided on the sterile isolation seat 30; the sterile isolation seat 30 is provided with a second through hole which is rotatably and cooperatively connected with the second body 801; a second body 801 is mounted in the second through hole; and an end of the second body 801 close to the instrument seat 20 is provided with a first groove 805 cooperating with the first protrusion. With a cooperation of the first protrusion 901 with the first groove 805, a relative motion between the first body 903 and the second body 801 is avoided, that is, a relative motion between the first coupling 90 and the second coupling 80 is avoided, such that the second coupling 80 delivers power to the transmission means 10 through the first coupling 90.

In the embodiment shown in FIG. 4, the second protrusion 803 is provided at a tail end of the second body 801 close to the motor mounting seat 40, and the second protrusion 803 has edges and corners, that is, the second protrusion 803 is of a non-cylindrical shape, and the specific shape of the second protrusion is preferably in-line, equilateral polygonal shape, etc. The second protrusion is mainly configured to deliver power, therefore, the shape of the second protrusion is within the protection scope of the present invention as long as the second protrusion 803 can prevent the second coupling 80 and the third coupling 70 from rotating relative to each other.

Figure 5:
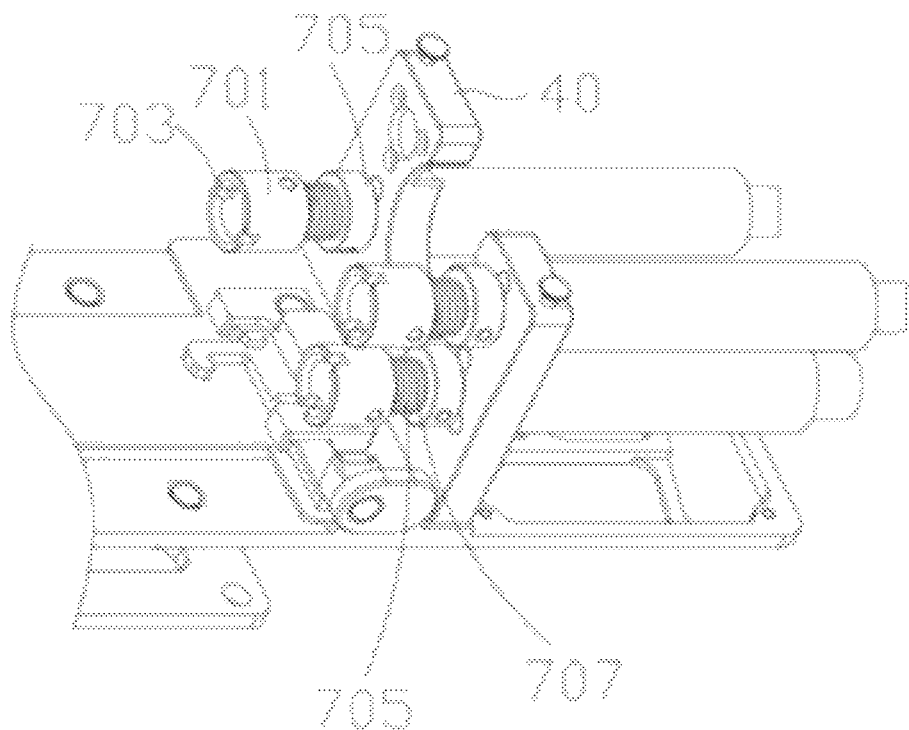
FIG. 5 is a structural schematic view of a third coupling of an operation instrument for an operation robot.

In the embodiment shown in FIG. 5, the third coupling 70 includes a third body 701, and an end of the third body 701 close to the sterile isolation seat 30 is provided with a second groove 703 cooperating with the second protrusion 803. With a cooperation of the second protrusion 803 with the second groove 703, a relative motion between the second body 801 and the third body 701 is avoided, that is, a relative motion between the second coupling 80 and the third coupling 70 is avoided, such that the third coupling 70 delivers the power provided by the driving means 50 to the transmission means 10 through the second coupling 80 and the first coupling 90.

In the embodiment shown in FIG. 5, the third coupling 70 further includes a connecting shaft 705 and an elastomer 707. One end of the connecting shaft 705 is connected to the driving means 50 and the other end is connected to the third body 701. The motor mounting seat 40 is provided with a third through hole rotatably and cooperatively connected with the connecting shaft 705; the connecting shaft 705 is mounted in the third through hole. One end of the elastomer 707 is clamped to the third body 701, and the other end is clamped to the connecting shaft 705. The connecting shaft 705 is of a stepped shape, and a large end of the connecting shaft 705 is mounted in the third through hole. The specific structure of the connecting shaft 705 is already known in the prior art and will not be described in detail here; the elastomer 707 includes a spring, one end of the spring abuts against the third body 701, and the other end abuts against the large end of the connecting shaft 705; and a stable cooperation among the first coupling 90, the second coupling 80 and the third coupling 70 is ensured effectively by a thrust provided by the spring, so that a stable power transmission is achieved.

In one embodiment, the first body 903, the second body 801 and the third body 701 are all of a cylindrical shape, and the first body 903, the second body 801 and the third body 701 are provided coaxially. Please note that, a case that the first body 903, the second body 801 and the third body 701 are of a cylinder shape is also within the protection scope of the present invention.

In at least one embodiment, the first protrusion 901 and the second protrusion 803 are both straight-shaped protrusions, and the first groove 805 and the second groove 703 are both straight-shaped grooves. The protrusions and the grooves with the above structure have a stable transmission and a low manufacturing cost and are assembled conveniently.

Figure 6:
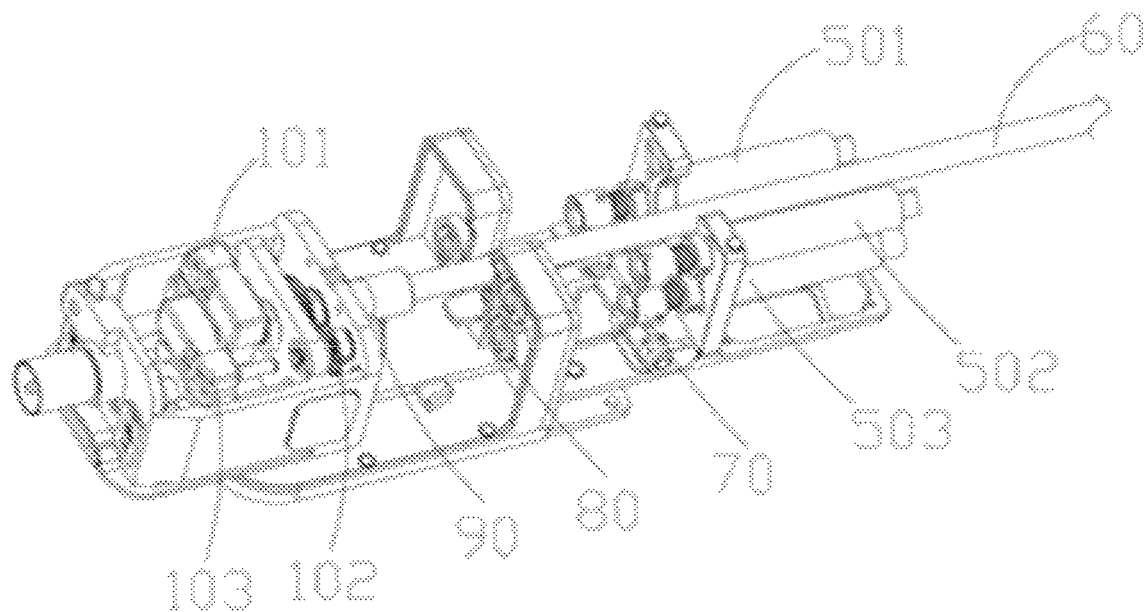
FIG. 6 is a backward structural exploded view of an operation instrument.
Figure 7:
FIG. 7 is a structural schematic view of an operation instrument, with the operation instrument for an operation robot being assembled.
Figure 8:
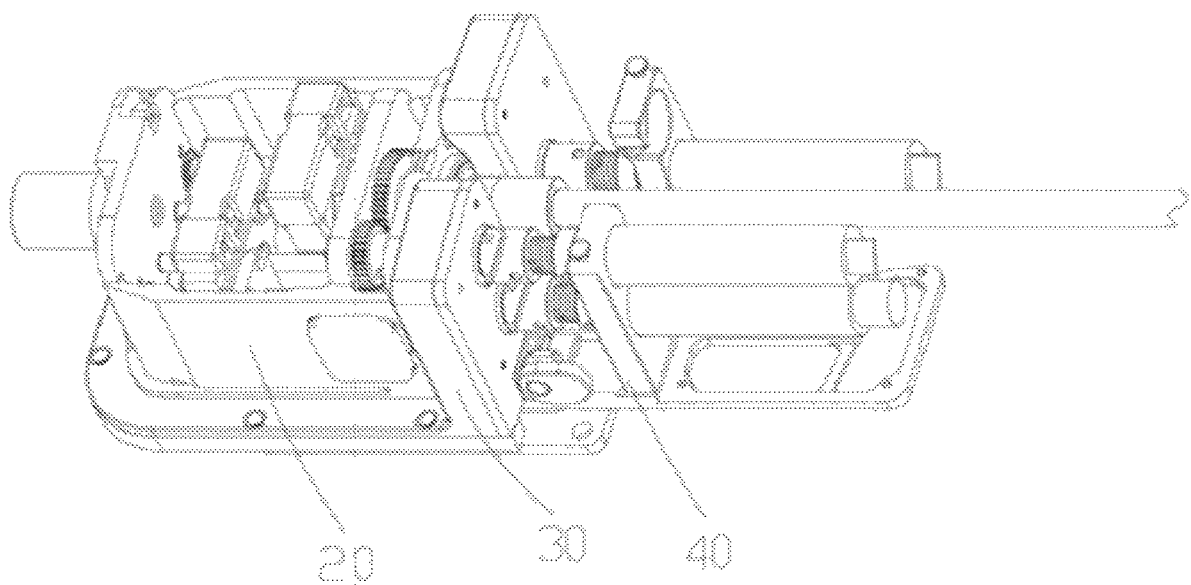
FIG. 8 is a structural schematic view of a mounting frame of an operation instrument.

In the embodiment shown in FIG. 6, the first coupling 90, the second coupling 80 and the third coupling 70 constitute a coupling group, and the operation instrument assembly for the operation robot includes three coupling groups. The operation instrument assembly for an operation robot includes three transmission means 10 and three driving means 50; the three transmission means 10 are correspondingly connected with three first couplings 90 in the three coupling groups, and the three driving means 50 are correspondingly connected with the three third couplings 70 in the three coupling groups. Specifically, the first coupling 90, the second coupling 80 and the third coupling 70 each are in the number of three; the three first couplings 90 are coaxially provided with the corresponding three second couplings 80, and the three second couplings 80 are coaxially provided with the corresponding three third couplings 70. The three driving means 50 are a first driving means 501, a second driving means 502 and a third driving means 503 respectively; the three transmission means 10 are a first transmission means 101, a second transmission means 102 and a third transmission means 103 respectively; the three driving means 50 are connected with the corresponding three transmission means respectively through the corresponding first coupling 90, second coupling 80 and third coupling 70, so as to deliver the power from the driving means to the transmission means, thus achieving the motion of the operation execution assembly 100 in at least 3 degrees of freedom.

II. Mounting Structure of the Instrument Seat 20 and the Sterile Isolation Seat 30

To allow the instrument seat to cooperate with the sterile isolation seat and thus connect the first coupling 90 provided on the instrument seat to the second coupling 80 provided on the sterile isolation seat, a quick mounting structure is provided between the instrument seat and the sterile isolation seat.

In the embodiment shown in FIGS. 8-11, the instrument seat 20 is provided with a slot component 201, and the sterile isolation seat 30 is provided with a block component 301 that is clamped into the slot component 201. It is worth noting that, a case that the slot component 201 is provided on the sterile isolation seat 30 and the block component 301 is provided on the instrument seat 20 is also within the protection scope of the present invention.

In one embodiment, the block component 301 is clamped into the slot component 201 to limit the degrees of freedom of the instrument seat 20 in 6 directions, where the degrees of freedom in 6 directions here refer to degrees of freedom in 6 directions which are up, down, left, right, front and rear. That is, the clamping-type components of the instrument seat 20 and the sterile isolation seat 30 of the present invention cooperate with each other to achieve a fixed connection of the instrument seat 20 and the sterile isolation seat 30, thereby achieving a quick assembling and disassembling of the instrument seat 20.

In the following embodiment, detailed descriptions are provided referring to the case that the slot component 201 is provided at the instrument seat 20 and the block component 301 is provided at the sterile isolation seat 30.

Figure 9:
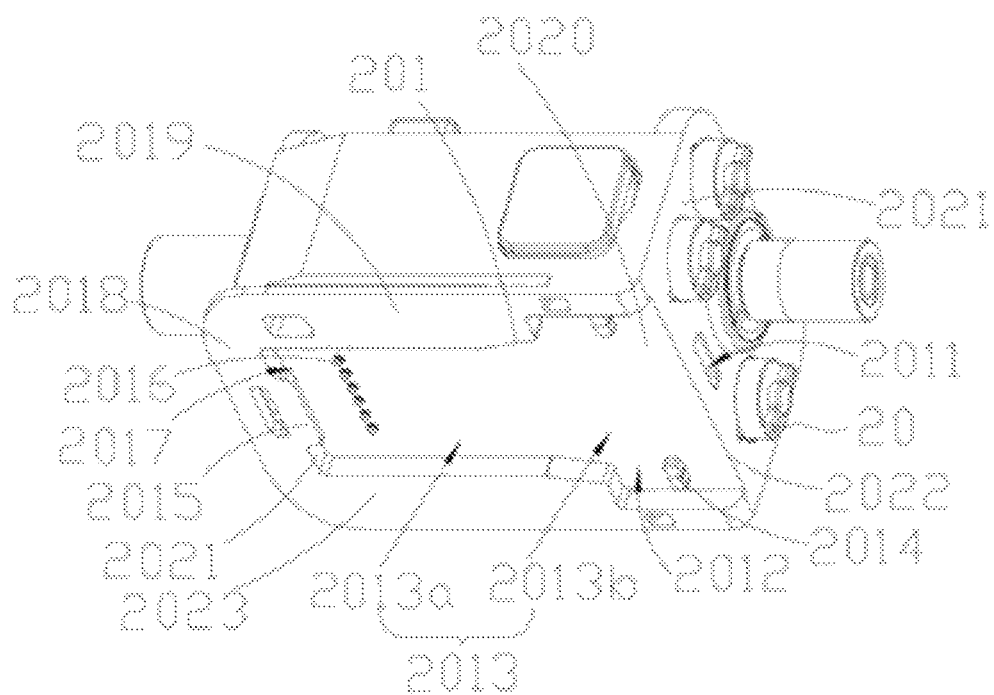
FIG. 9 is a schematic view of a slot component on the instrument seat.

As shown in FIG. 9, the slot component 201 includes a position-limiting slot 2013; and the position-limiting slot 2013 includes a closed end 2021 and an open end 2022 extending to an edge of the instrument seat 20. The instrument seat 20 has a bottom face 2020 and a first side face 2021; the bottom face 2020 of the instrument seat is provided with a first protruding edge 2019, a second protruding edge 2018 and a third protruding edge 2023, where the first protruding edge 2019, the second protruding edge 2018 and the third protruding edge 2023 are connected in sequence to form the position-limiting slot 2013 with an opening.

Figure 10:
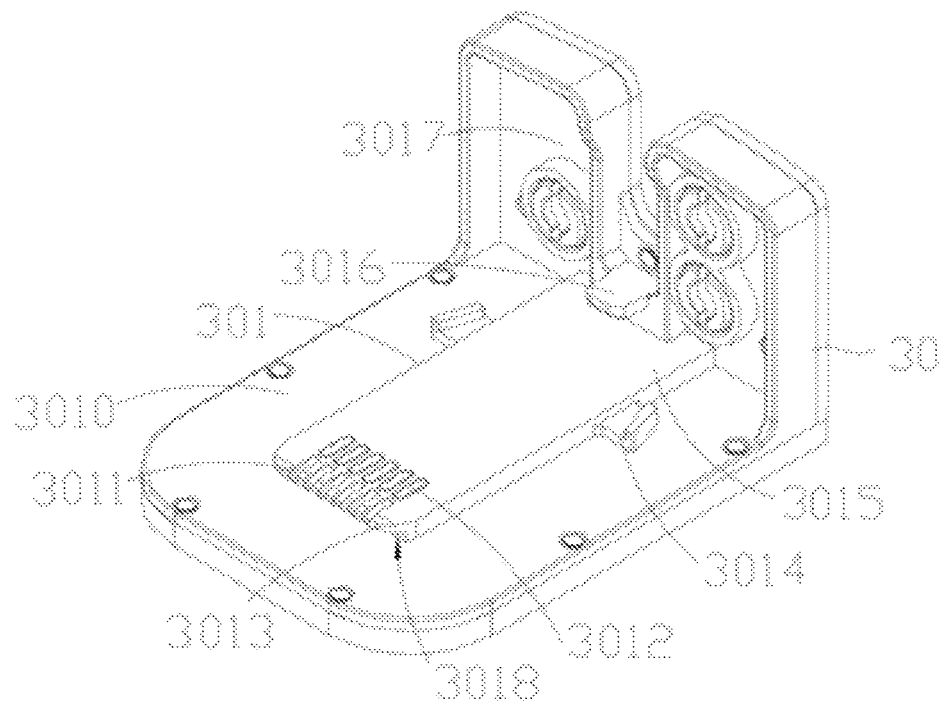
FIG. 10 is a schematic diagram of a block component on the sterile isolation seat.

As shown in FIG. 10, the sterile isolation seat 30 is of an L-shape; the sterile isolation seat 30 has an upper surface 3010 and an inner side face 3017; and the block component 301 includes a boss 3015. The boss 3015 is provided on the upper surface 3010 of the sterile isolation seat, the cross-sectional area of the boss 3015 is smaller than the area of the upper surface 3010 of the sterile isolation seat, and the boss 3015 and the upper surface 3010 of the sterile isolation seat form a step.

In some example embodiments, the cross section of the boss 3015 is of a rectangular shape. It is particularity noted that the shape of the cross section here is defined in accordance with the position-limiting slot 2013 into which the boss 3015 can extend from the opening of the position-limiting slot 2013. It is within the protection scope of the present invention, as long as the shape of the cross section of the boss 3015 allows the boss 3015 to extend into the position-limiting slot 2013 from the opening of the position-limiting slot 2013.

After the instrument seat 20 and the sterile isolation seat 30 are mounted, the three side faces of the boss 3015 abut against the third protruding edge 2023, the second protruding edge 2018 and the first protruding edge 2019, respectively, that is, the boss 3015 is clamped into the position-limiting slot 2013. The degrees of freedom of the boss 2015 in the front and rear directions are limited by the third protruding edge 2023 and the first protruding edge 2019, thereby limiting the degrees of freedom of the instrument seat 20 in the front and rear directions, that is, avoiding a forward and backward displacement of the instrument seat 20 relative to the sterile isolation seat 30.

As shown in FIG. 9, the slot component also includes a positioning block 2015, and the positioning block 2015 is provided at one side of the second protruding edge 2018 close to the position-limiting slot 2013, that is, the positioning block 2015 is located at the closed end 2021 of the position-limiting slot. There is a gap between the positioning block 2015 and the bottom face 2020 of the instrument seat, and a first positioning slot 2107 is formed between the positioning block 2015 and the bottom face 2020 of the instrument seat.

As shown in FIG. 10, the block component 301 further includes a protruding block 3013, and the protruding block 3013 is provided in a protruding manner on an end of the boss 3015 away from the inner side face 3017 of the sterile isolation seat; there is a gap between the protruding block 3013 and the upper surface 3010 of the sterile isolation seat; and a second positioning slot 3018 is formed between the protruding block 3013 and the upper surface 3010 of the sterile isolation seat.

In some example embodiments, a distance between the positioning block 2015 and the bottom face 2020 of the instrument seat is equal to a thickness of the protruding block 3013, and a distance between the protruding block 3013 and the upper surface 3010 of the sterile isolation seat is equal to a thickness of the positioning block 2015.

As shown in FIGS. 9-10, the slot component 201 includes a through slot 2011, and the through slot 2011 is provided at a first side face 2021 of the instrument seat and is located above an open end 2022; and the block component 301 further includes a position-limiting block 3016 provided at the inner side face 3017 of the sterile isolation seat, and the position-limiting block 3016 contacts and cooperates with the instrument seat 20 at an inner wall of the through slot 2011.

After the instrument seat 20 and the sterile isolation seat 30 are mounted, the position-limiting block 3016 is clamped into the through slot 2011, the protruding block 3013 is clamped into the first positioning slot 2107, and the positioning block 2015 is clamped into a second positioning slot 3018, so as to limit the degree of freedom of the instrument seat 20 or the sterile isolation seat 30 in the up and down directions, that is, avoid a displacement of the instrument seat 20 relative to the sterile isolation seat 30 in the up and down directions.

As shown in FIG. 9, a side of the first protruding edge 2019 close to the third protruding edge 2023 is of a stepped shape, and a side of the third protruding edge 2023 close to the first protruding edge 2019 is also of a stepped shape That is, the position-limiting slot 2013 formed by the first protruding edge 2019, the second protruding edge 2018 and the third protruding edge 2023 includes a front segmental position-limiting slot 2013b and a rear segmental position-limiting slot 2013a. A distance between the first protruding edge 2019 and the third protruding edge 2023 at the front segmental position-limiting slot 2013b is larger a distance therebetween at the rear segmental position-limiting slot 2013a, the opening of the position-limiting slot 2013 is located at the front segmental position-limiting slot 2013b, and a stepped face (not marked in the figure) is formed at the junction of the front segmental position-limiting slot 2013b and the rear segmental position-limiting slot 2013a.

The slot component 201 further includes two projections 2014. The two projections 2014 are provided at a bottom face 2020 of the instrument seat, the two projections 2014 are both provided in the front segmental position-limiting slot 2013b, and a recess 2012 is formed between each of the two projections 2014 and the corresponding stepped face (not marked in the figure).

In some example embodiments, two projections 2014 are located on two sides of the rear segmental position-limiting slot 2013a, and a distance between the two projections 2014 is larger than a distance between the first protruding edge 2019 and the third protruding edge 2023 at the rear segmental position-limiting slot 2013a.

As shown in FIG. 10, the block component 301 further includes two stops 3014, and the two stops 3014 are provided on two sides of the boss 3015 in contact with the third protruding edge 2023, respectively. After the instrument seat 20 and the sterile isolation seat 30 are mounted, the two stops 3014 are clamped into the corresponding recess 2012 respectively, and one end of the stop 3014 contacts and cooperates with the stepped face (not marked in the figure), and the other end contacts and cooperates with the projection 2014, so as to limit the degrees of freedom of the instrument seat 20 or the sterile isolation seat 30 in left and right directions, i.e., avoid a displacement of the instrument seat 20 relative to the sterile isolation seat 30 in left and right directions.

In some example embodiments, a distance between the two projections 2014 is larger than a distance between the first protruding edge 2019 and the third protruding edge 2023 at the rear segmental position-limiting slot 2013a, so as to facilitate the boss 2015 to be clamped into the rear segmental position-limiting slot 2013a; and a thickness of the projection 2014 is smaller than a depth of the position-limiting slot 3013, so as to facilitate the stop 3014 to be clamped into the recess 2012.

Figure 11:
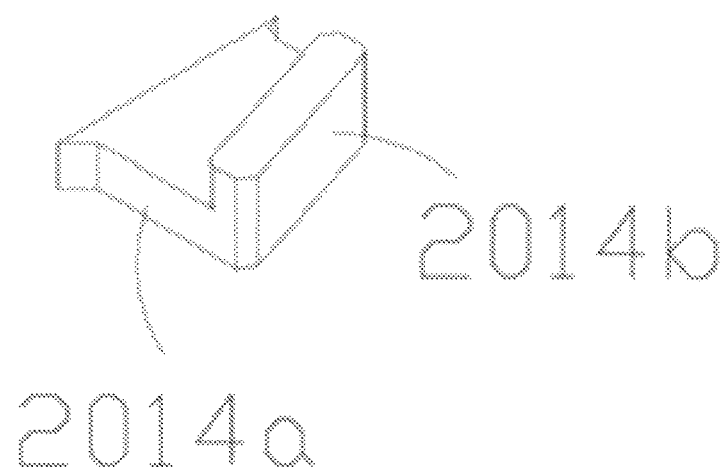
FIG. 11 is a structural schematic view of a stop.

As shown in FIGS. 9-11, there is a channel between the first protruding edge 2019 and the third protruding edge 2023 and the corresponding projections 2014 (not marked in the FIG.); the stop 3014 includes a bottom plate 3014a connected with the boss 3015, the bottom plate 3014a is provided thereon with a side plate 3014b. The side plate 3014b and the boss 3015 form an angle, i.e., the side plate 3014b and the boss 3015 form a horn opening, to facilitate the side plate 3014b to be clamped from the channel into the recess 2012.

The bottom face 2020 of the instrument seat is provided with a plurality of communicating-interface copper blocks 2016, and the plurality of communicating-interface copper blocks 2016 are located within the position-limiting slot 2013; and the sterile isolation seat 30 is provided on the boss 3015 with a plurality of contacts 3012 corresponding to the communicating-interface copper blocks 2016.

In some example embodiments, the protruding block 3013 is provided with guide slots 3011, so that the communicating-interface copper blocks 2016 slides to the contacts 3012 along the guide slots 3011, effectively avoiding the damage to the communicating-interface copper block 2016.

Thus, with the above structure, the instrument seat 20 and the sterile isolation seat 30 can be readily connected detachably and are electrically connected while being mechanically connected.

III. The Connecting Structure of the Sterile Isolation Seat and the Motor Mounting Seat A quick mounting structure is provided between the sterile isolation seat 30 and the motor mounting seat 40, to deliver power of the motor provided on the motor mounting seat to the transmission means 10 through the couplings 70, 80, and 90. On the other hand, an electrical connection is achieved among the instrument seat 20, the sterile isolation seat 30 and the motor mounting seat 40.

Figure 12:
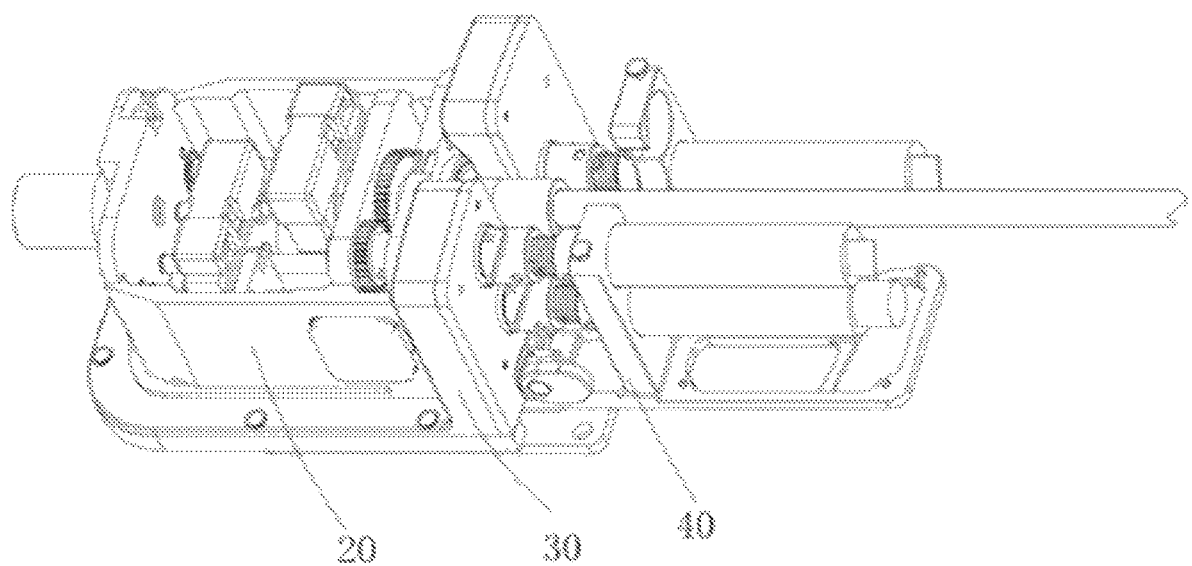
FIG. 12 is a structural schematic view of a connecting means of the surgical instrument.
Figure 13:
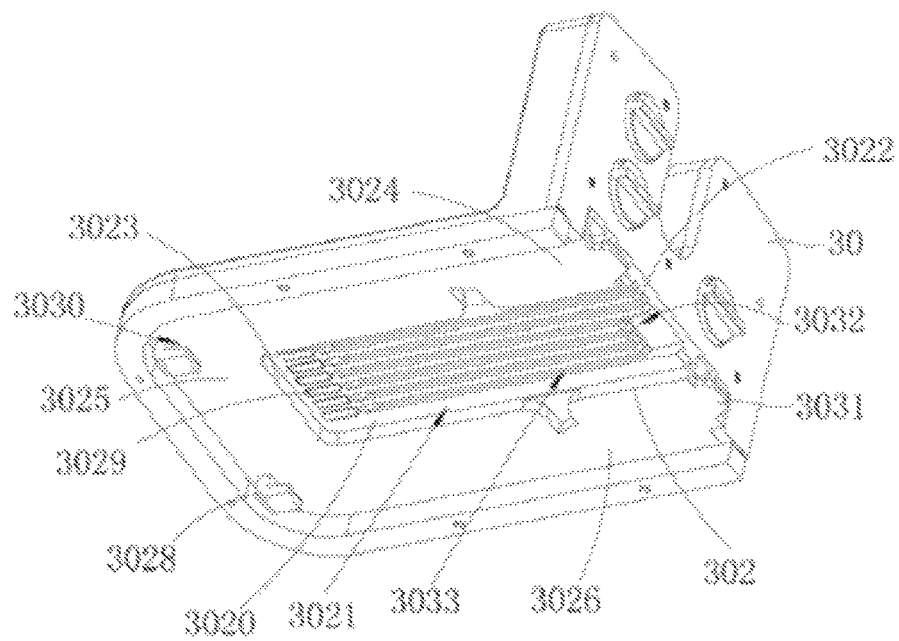
FIG. 13 is a schematic view of a slot component on the sterile isolation seat.
Figure 14:
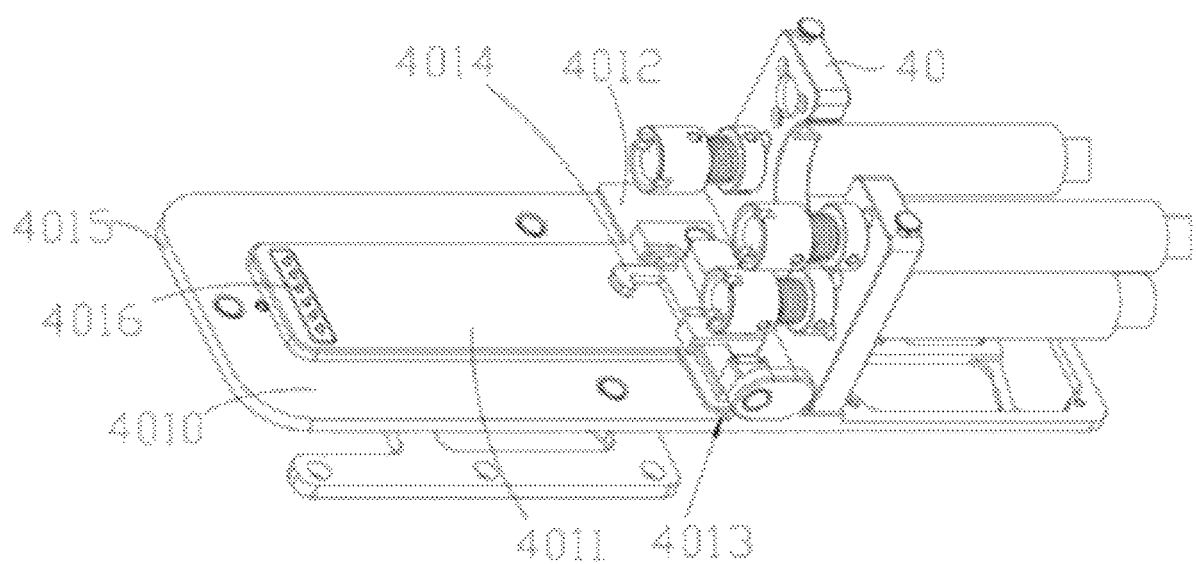
FIG. 14 is a schematic view of a block component on the motor mounting seat.

As shown in FIGS. 12-14, the sterile isolation seat 30 is provided with a slot component 302 on its lower side, and the motor mounting seat 40 is provided with a block component that is clamped into the slot component 302. It is worth noting that, a case that the slot component 302 is provided on the motor mounting seat 40 and the block component is provided on the sterile isolation seat 30, is also within the protection scope of the present invention.

In the following embodiment, detailed descriptions are provided by the slot component provided on the sterile isolation seat 30 and the block component provided on the motor mounting seat 40.

In the embodiment, the block component 401 is clamped into the slot component 302 to limit the degrees of freedom of the sterile isolation seat 30 in 6 directions, where the degrees of freedom in 6 directions here refer to degrees of freedom in 6 directions which are up, down, left, right, front, and rear. That is, the clamping-type components of the motor mounting seat 40 and the sterile isolation seat 30 of the present invention cooperate with each other to achieve a fixing of the sterile isolation seat 30 at the motor mounting seat 40, thereby achieving a quick assembling and disassembling of the sterile isolation seat 30.

As shown in FIG. 13, the slot component 302 includes a position-limiting slot 3021; the position-limiting slot 3021 includes a closed end 3020 and an open end 3022 extending to an edge of the sterile isolation seat 30. The sterile isolation seat 30 has a bottom face 3023; the bottom face 3023 of the sterile isolation seat is provided with a first protruding edge 3024, a second protruding edge 3025 and a third protruding edge 3026, where the first protruding edge 3024, the second protruding edge 3025 and the third protruding edge 3026 are connected in sequence to form the position-limiting slot 3027 with an opening.

As shown in FIG. 14, the block component includes a boss 4011; the motor mounting seat 40 has an upper surface 4010; the boss 4011 is fixed at an upper surface 4010 of the motor mounting seat; the cross-sectional area of the boss 4011 is smaller than an area of the upper surface 4010 of the motor mounting seat; and the boss 4011 and the upper surface 4010 of the motor mounting seat form a step.

In preferred examples of some embodiments, the cross section of the boss 4011 is of a rectangular shape. It is particularity noted that the shape of the cross section here is defined in accordance with the position-limiting slot 3011 into which the boss 4011 can extend from the opening of the position-limiting slot 3011. It is within the protection scope of the present invention as long as the shape of the cross section of the boss 4011 allows the boss 4011 to extend into the position-limiting slot 3011 from the opening of the position-limiting slot 3027.

After the sterile isolation seat 30 and the motor mounting seat 40 are mounted, the three side faces of the boss 4011 abut against the first protruding edge 3024, the second protruding edge 3025 and the third protruding edge 3026, respectively, that is, the boss 4011 is clamped into the position-limiting slot 3027. The degrees of freedom of the boss 4011 in the front and rear directions are limited by the first protruding edge 3024 and the third protruding edge 3026, thereby limiting the degrees of freedom of the sterile isolation seat 30 in the front and rear directions, that is, avoiding a forward and backward displacement of the sterile isolation seat 30 relative to the motor mounting seat 40.

As shown in FIG. 13, the slot component 302 further includes at least one L-shaped positioning block 3028, the L-shaped positioning block 3028 is provided at the second protruding edge 3025, that is, the L-shaped positioning block 3028 is close to an end 3020 of the closed end. A first positioning slot 3030 is formed between the L-shaped positioning block 3028 and the second protruding edge 3025, with the opening of the first positioning slot 3030 facing the position-limiting slot 3027.

As shown in FIG. 14, the block component 401 also includes a bottom plate 4015 of the motor mounting seat. After the sterile isolation seat 30 and the motor mounting seat 40 are mounted, the bottom plate 4015 of the motor mounting seat is clamped into the first positioning slot 3017, that is, the bottom plate 4015 of the motor mounting seat contacts and cooperates with each of the L-shaped stop 3028 and the second protruding edge 3025.

As shown in FIG. 13, the slot component 302 also includes two second positioning blocks 3031. The two second positioning blocks 3031 are provided on the first protruding edge 3024 and the third protruding edge 3026, respectively; and the two second positioning blocks 3031 are located at an end of the first protruding edge 3024 or the third protruding edge 3026 close to the opening of the position-limiting slot 3027.

As shown in FIG. 14, the block component 401 also includes two position-limiting plates 4012, the two position-limiting plates 4012 are fixed on two sides of the boss 4011 respectively, and a second positioning slot 4013 is formed between each of the two position-limiting plates 4012 and the upper surface 4010 of the motor mounting seat. After the sterile isolation seat 30 and the motor mounting seat 40 are mounted, the second positioning block 3031 is clamped into the second positioning slot 4013, and the motor mounting seat 40 is clamped into the first positioning slot 3030 to limit the degrees of freedom of the sterile isolation seat 30 in up and down directions, that is, avoiding a displacement of the sterile adapter 20 relative to the motor mounting seat 40 in up and down directions. As shown in FIG. 3, the block component 401 further includes an L-shaped barb 4014, the L-shaped barb 4014 is provided on the motor mounting seat 40, and the L-shaped barb 4014 is located above the boss 4011.

As shown in FIG. 13, the slot component 302 also includes an L-shaped barb slot 3032, the bottom face 3023 of the sterile isolation seat 30 is provided with a mounting slot (not marked in the FIG.) at the opening of the position-limiting slot 3027, and the sterile isolation seat is provided with a protrusion (not marked in the FIG.) in the mounting slot to form the L-shaped barb slot 3032. After the sterile isolation seat 30 and the motor mounting seat 40 are mounted, the L-shaped barb 4014 is clamped into the L-shaped barb slot 3032, thereby limiting the degrees of freedom of the sterile isolation seat 30 in the front and rear directions, that is, avoiding a left and right displacements of the sterile isolation seat 30 relative to the motor mounting seat 40.

As shown in FIGS. 13-14, a plurality of communicating-interface copper blocks 4016 are provided on the boss 4011, and the plurality of communicating-interface copper blocks 4016 are provided to be evenly spaced; the sterile isolation seat 30 is provided with a plurality of contacts 3029 corresponding to the communicating-interface copper block 4016 in the position-limiting slot 3027. The sterile isolation seat 30 is provided with a guide slot 3033 on the bottom face of the position-limiting slot 3011, so that the communicating-interface copper blocks 4016 slides to the contacts 3029 along the guide slot 3033, achieving mechanical and electrical connections between the sterile isolation seat 30 and the motor mounting seat 40.

IV. Driving of the Operation Execution Assembly 100

The instrument seat 20 includes a housing 200, and a first actuating assembly 202 provided within the housing; the first actuating assembly 202 receives power delivered from the driving means through the couplings 70, 80 and 90. Said first actuating assembly 202 includes a first screw 203 and a first nut slider 204 cooperating with each other, that is, the first nut slider 204 is sleeved on the first screw 203, and the first nut slider 204 is in threaded and cooperative connection with the first screw 203; the first screw 203 is rotatably mounted on a bracket 207, and the bracket 207 is provided with a guide position-limiting rod 205 that limits the rotation of the first nut slider 204. Specifically, the first nut slider 204 is provided with a guide hole, the guide position-limiting rod 205 passes through the guide hole and contacts and cooperates with the first nut slider 204. When the first screw 203 is rotated by means of thread, since the first nut slider 204 is cooperated with the first screw 203 by means of the thread and is limited by the guide position-limiting rod 205, the first nut slider 204 moves along the guide position-limiting rod 205 (the first screw 203).

Figure 21:
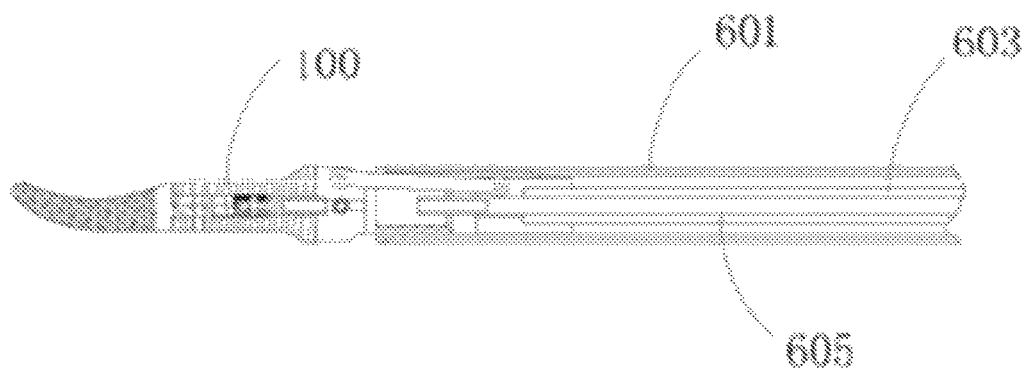
FIG. 21 is a structural schematic view of a control assembly of an operation instrument.
Figure 22:
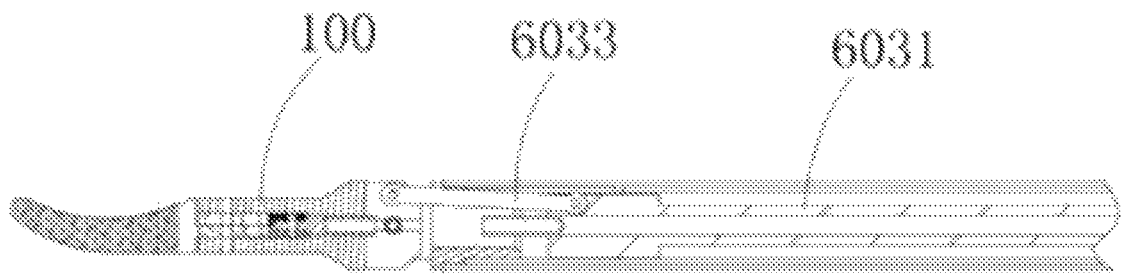
FIG. 22 is a structural schematic view of a first transmission member of an operation instrument.
Figure 23:
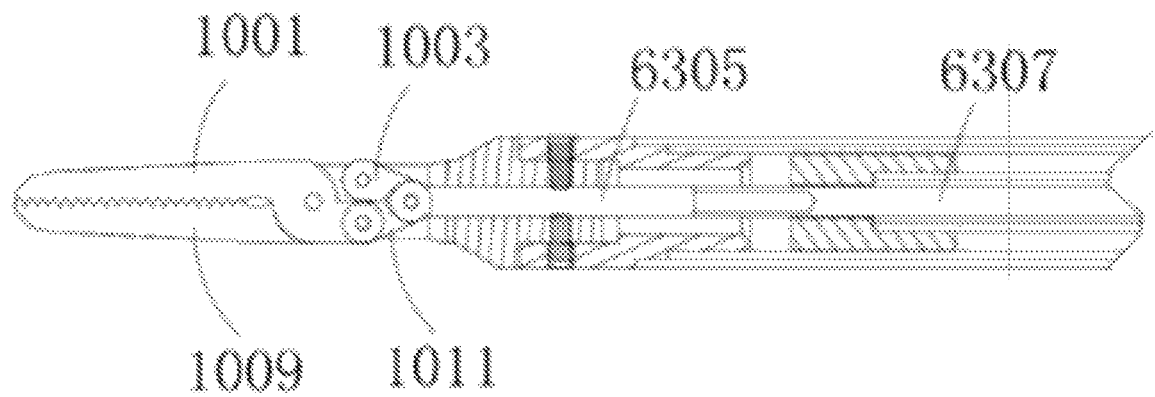
FIG. 23 is a structural schematic view of an execution assembly and a third transmission member of an operation instrument.

In the embodiment shown in FIG. 21, the control assembly 60 includes a second transmission member 601 and a first transmission member 603, and the execution assembly 100 is hingedly provided on the second transmission member 601. In the embodiment shown in FIG. 8, the first transmission member 603 includes a first transmission rod 6031 connected with the first nut slider 204, and a movable rod 6033 is provided between the other ends of the first transmission rod 6031 and the execution assembly 100. One end of the movable rod 6033 is rotatably connected with the first transmission rod 6031, and the other end is rotatably connected with the execution assembly 100, and the manner where the movable rod 6033 is connected with each of the first transmission rod 6031 and the execution assembly 100 includes but not limited to a pin connection. When the first screw 203 rotates, the first nut slider 204 is actuated to reciprocate, and the first nut slider 204 actuates the first transmission rod 203 to reciprocate, so that the movable rod 6033 pushes the execution assembly 100 to bend or straighten at the place where the execution assembly 100 is hinged, thereby achieving the bending and straightening of the execution assembly 100 at a wrist joint, such that the execution assembly 100 implements a wrist joint action similar to that of a human hand, achieving the effect of synchronizing the manipulation of the operation instrument and the human hand, and reducing the difficulty of the manipulation of the operation instrument.

Figure 16:
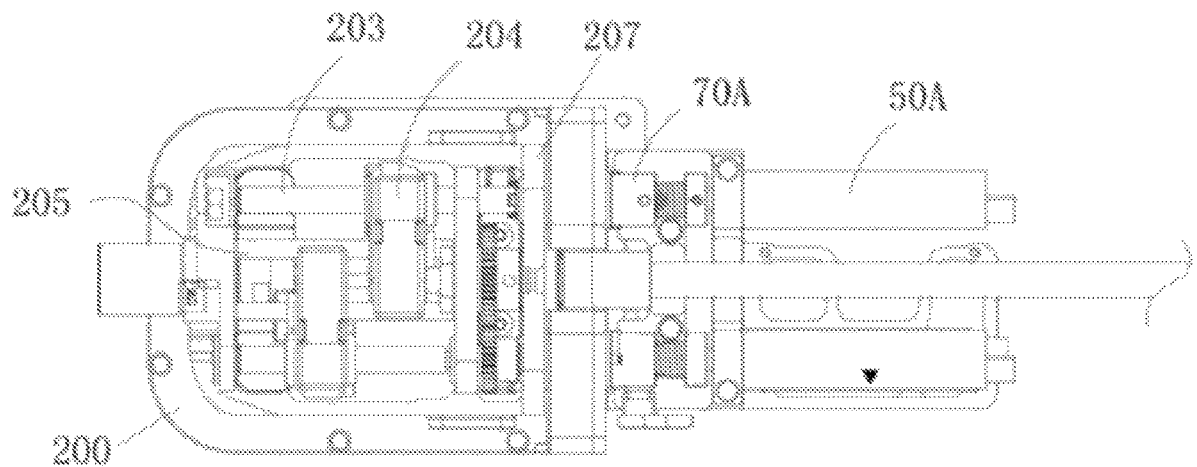
FIG. 16 is a structural schematic view of a first actuating assembly of an operation instrument.

In the embodiment shown in FIG. 16, the first driving assembly 50A includes a first motor 501A, and the first motor 501A is connected with the first screw 203 through a first coupling 70A, a second coupling 80A and a third coupling 90A. The first coupling 90A is rotatably mounted on a mounting bracket 207, and the first motor 501A is fixedly mounted on the motor mounting bracket 40. The first motor 501A works to actuate the first screw 203 to rotate, so that the first nut slider 204 reciprocates A protective casing is provided outside the first motor 501A, and the protective casing may also prevent bacteria from growing.

Figure 15:
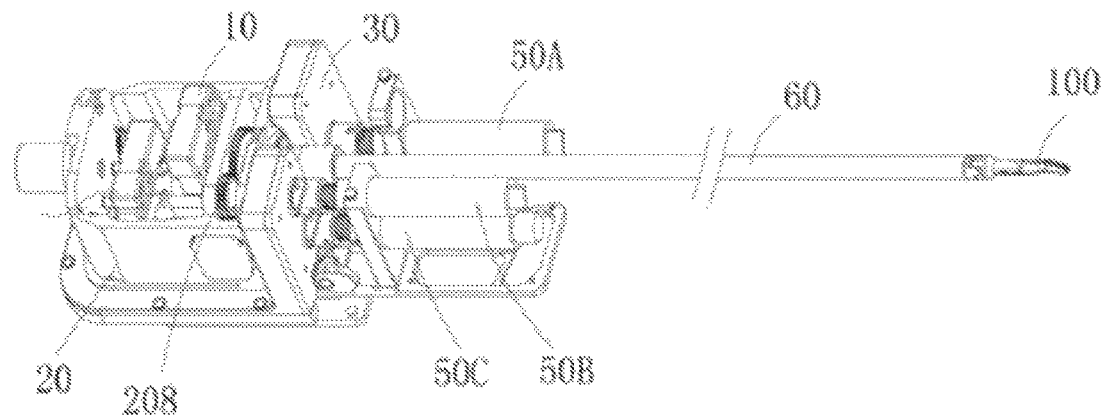
FIG. 15 is a structural schematic view of an operation instrument.
Figure 17:
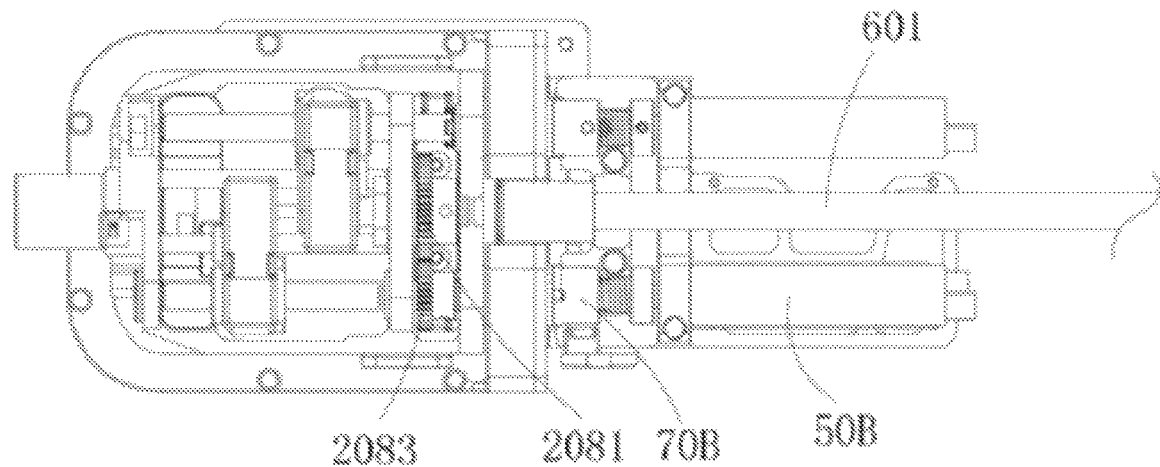
FIG. 17 is a structural schematic view of a second actuating assembly of an operation instrument.

In the embodiment shown in FIGS. 15 and 17, the instrument seat 20 further includes a second actuating assembly 208 and a second driving assembly 50B, and the second actuating assembly 208 includes a master gear 2083 and a slave gear 2081 that mesh with each other. The second driving assembly 50B includes a second motor 501B, the second motor 501B is connected with the master gear 2083 through a first coupling 70B, a second coupling 80B and a third coupling 90B; the slave gear 2081 is fixedly provided on the second transmission member 601. The master gear 2083 is firstly driven to rotate, and the master gear 2083 actuates the slave gear 2081 to rotate, so as to cause the second transmission member 601 fixed on the slave gear 2083 to rotate and actuate the execution assembly 100 to rotate, so that the operation execution assembly 100 can quickly and accurately complete the instructions issued by the doctor in a limited space, ensuring the smooth progress of the operation, and also improving the versatility of operation instruments of the operation robot.

In one embodiment, the second coupling 90B is rotatably mounted on the mounting bracket 507, and the second motor 501B is fixedly mounted on the motor mounting seat 40. A protective casing is provided outside the second motor 501B, and the protective casing may also prevent bacteria from growing.

Figure 24:
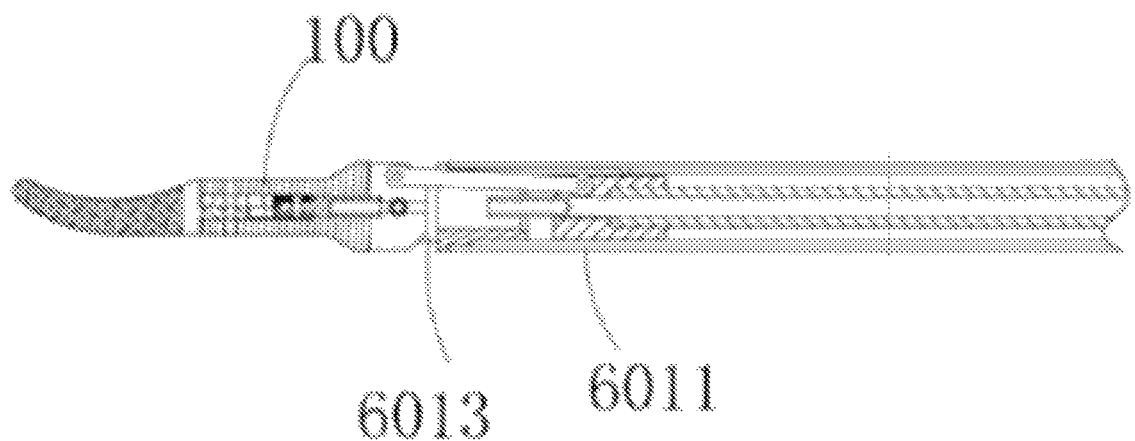
FIG. 24 is a structural schematic view of a second transmission member of an operation instrument.

In the embodiment shown in FIG. 24, the second transmission member 601 includes a second transmission rod 6011 and a connecting sleeve 6013, and the second transmission rod 6011 is fixedly connected with the connecting sleeve 6013. The execution assembly 100 is hinged with the connecting sleeve 6013 by a pin, so that the execution assembly 100 may rotate along the second transmission member 601 to achieve a wrist joint action; and the slave gear sleeve 2081 is fixedly provided on the second transmission rod 6011.

In the embodiment shown in FIGS. 15, 19, 21 and 23, the operation instrument further includes a third actuating assembly 206 and a third driving assembly 50C, and the third actuating assembly 206 includes a second screw 2063 and a second nut slider 2061 cooperating with each other;

the third driving assembly 50C is connected with the second screw 2063, wherein the third driving assembly 50C drives the second screw 2063 to rotate, so that the second nut slider 2061 reciprocates along the second screw 2063. The control assembly 60 also includes a third transmission member 605, and the third transmission member 605 includes: a three transmission rod 6307 that is rotatably connected with the second nut slider 2061, and a connecting rod 6305 connecting the third transmission rod 6307 and the execution assembly. The connecting rod 6305 is a flexible connecting rod, which may bear an axial force, and thus the connecting rod 6305 does not bend when bearing an axial force, and the connecting rod 6035 bends when bearing a radial force. Therefore, the connecting rod 6305 may achieve a reciprocated movement in an axial direction, and the connecting rod 6305 may bend due to the radial force when the execution assembly 100 needs to perform a wrist joint swing motion.

In one embodiment, the execution assembly 100 includes a first plier body 1001 and a second plier body 1009. The first plier body 1001 and the second plier body 1009 are provided in an intersecting manner, and the first plier body 1001 is rotatably connected with the second plier body 1009 by a pin at the intersecting area therebetween, that is, the first plier body 1001 and the second plier body 1009 may rotate in an intersecting manner along the pin, achieving the opening and closing of the first plier body 1001 and the second plier body 1009.

In one embodiment, the execution assembly 100 further includes a transition member, the transition member includes a first transition rod 1011 and a second transition rod 1003. One end of each of the first transition rod 1011 and the second transition rod 1003 is rotatably connected with the connecting rod 6305, the other end of the first transition rod 1011 is rotatably connected with the first plier body 1001, and the other end of the second transition rod 1003 is rotatably connected with the second plier body 1009, wherein the execution assembly 100 is opened or closed following the reciprocation of the third transmission rod 6307. First, the first plier body 1001 and second plier body 1009 are provided in an intersecting manner; then, a pin is inserted at the intersecting area of the first plier body 1001 and second plier body 1009, so that the first plier body 1001 and second plier body 1009 are rotatably connected with the pin; then, one end of each of the first transition rod 1011 and the second transition rod 1003 is rotatably connected with the connecting rod 6305; then, the other end of the first transition rod 1011 is rotatably connected with the first plier body 1001, and at the same time, the other end of the second transition rod 1003 is rotatably connected with the second plier body 1009, so that the first transition rod 1011, the second transition rod 1003, the first plier body 1001 and the second plier body 1009 form a quadrangle; thereafter, when the third transmission rod 6307 actuates the connecting rod 6305 to reciprocate, the first transition rod 1011 and the second transition rod 1003 are actuated to rotate, so that the first transition rod 1011 and the second transition rod 1003 push the first plier body 1001 and the second plier body 1009 to open or close, thereby actuating the operation instrument 100 to open or close, achieving the driving of the operation instrument 100.

Figure 19:
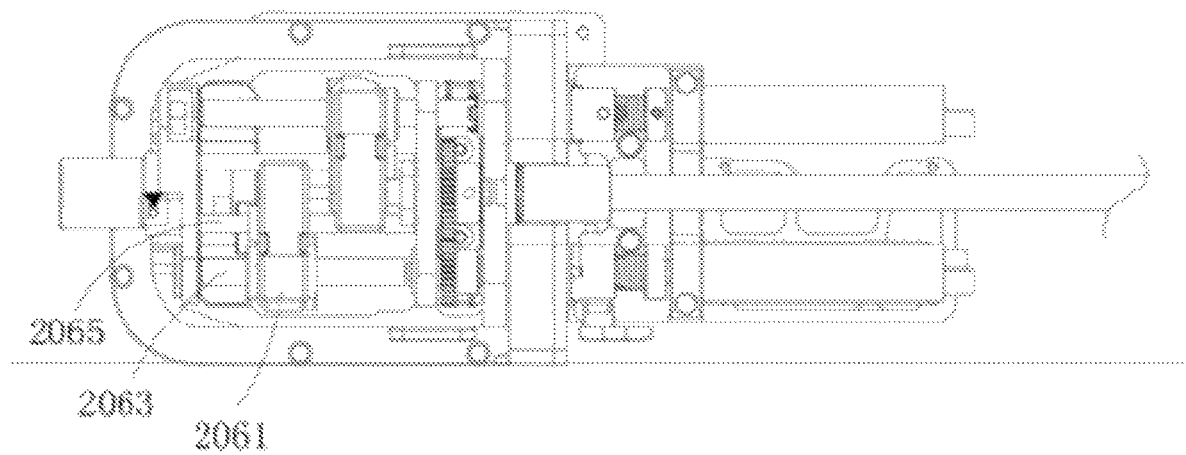
FIG. 19 is a structural schematic view of a third actuating assembly of an operation instrument.
Figure 20:
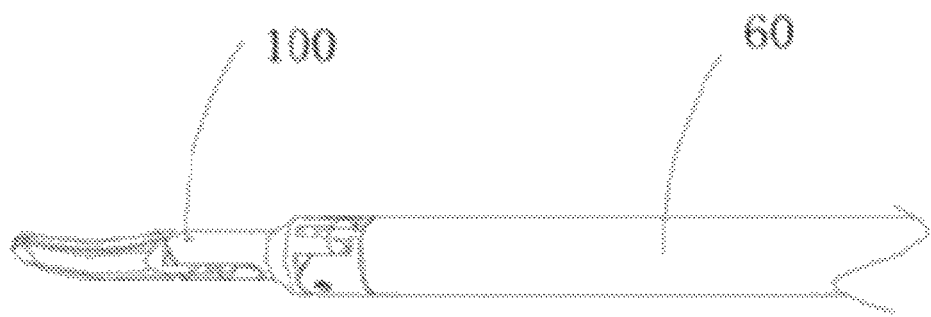
FIG. 20 is a schematic view of a cooperation of an execution assembly with a control assembly of an operation instrument.

In the embodiment shown in FIG. 19, the second nut slider 2061 is sleeved on the second screw 2063, and the second nut slider 2061 is in threaded and cooperative connection with the second screw 2063. The second screw 2063 is rotatably mounted on the mounting bracket 207, and the mounting bracket 207 is provided with a guide position-limiting rod 2065 that limits the rotation of the second nut slider 2061. Specifically, the second nut slider 2061 is provided with a position-limiting hole; the guide position-limiting rod 2065 passes through the position-limiting hole, and contacts and cooperates with the second nut slider 2061. When the second screw 2063 rotates by means of the thread, since the second nut slider 2061 cooperates with the second screw 2063 by means of the thread, and is limited by the guide position-limiting rod 2063, the second nut slider 2061 moves along the guide position-limiting rod 2065 (the second screw), thereby actuating the reciprocation of the third transmission rod 6307.

Figure 18:
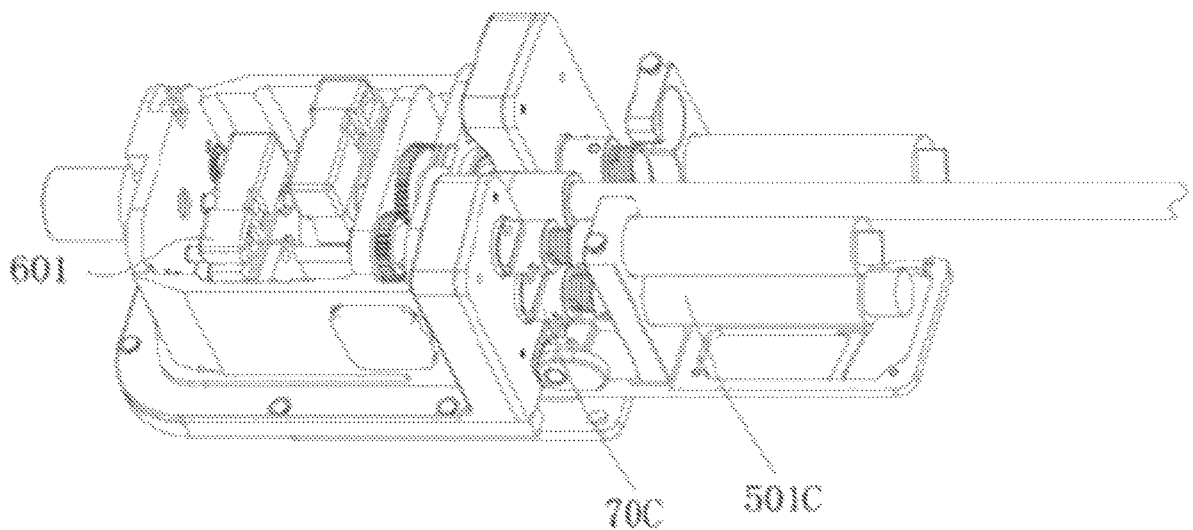
FIG. 18 is a perspective schematic view of a third actuating assembly of an operation instrument.

In the embodiment shown in FIG. 18, the third driving assembly 50C includes a third motor 501C, and the third motor 501C is connected with the second screw 2063 through the first coupling 70C, the second coupling 80C and the third coupling 90C. The third coupling 90C is rotatably mounted on the mounting bracket 207, and the third motor 501C is fixedly mounted on the motor mounting seat 40; and a protective casing is provided outside the third motor 501C, and the protective casing may also prevent bacteria from growing.

In one embodiment, the second transmission rod 6011 and the first transmission rod 6031 are both of a hollow structure, the first transmission rod 6031 is provided in the second transmission rod 6011, and the third transmission rod 6307 is provided in the first transmission rod 6031. The operation instrument 100 has a simple structure and can effectively reduce the volume of the operation instrument of the operation robot, so that the operation execution assembly can quickly and accurately complete the instructions issued by the doctor in a limited space.

V. Bayonet Structure and Control Assembly

Figure 26:
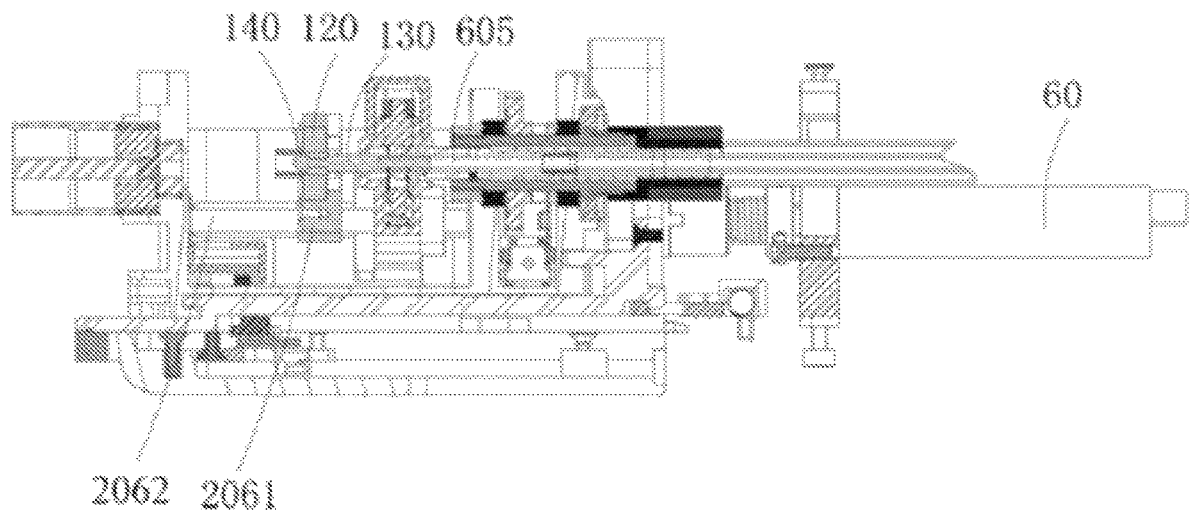
FIG. 26 is a schematic view of a bayonet structure of a needle holder.
Figure 27:
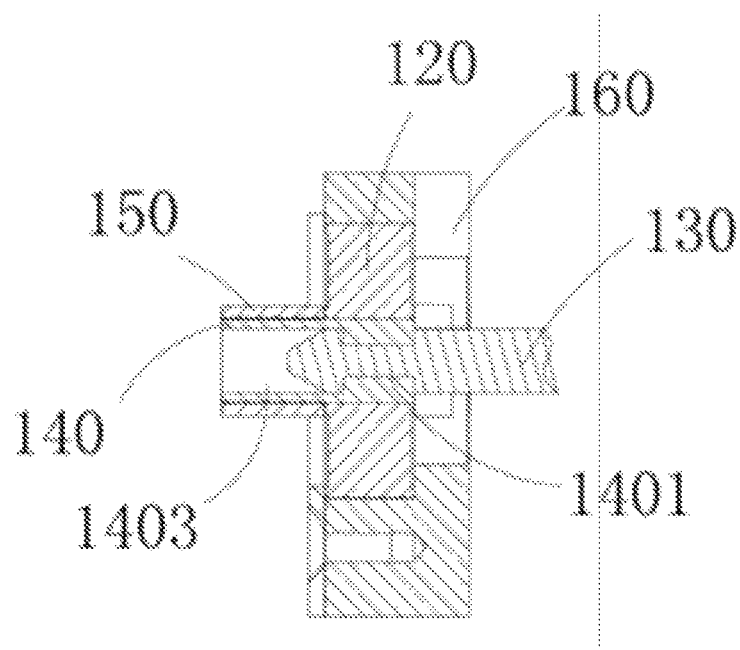
FIG. 27 is a partial schematic view of a bayonet structure of a needle holder.
Figure 28:
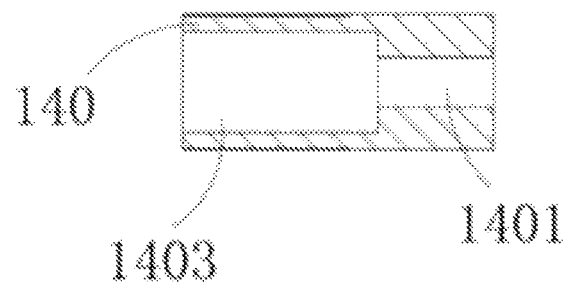
FIG. 28 is a structural schematic view of a bayonet sleeve of a bayonet structure of a needle holder.

In the embodiment shown in FIGS. 26-27, the embodiment of the present invention provides a bayonet structure, including a nut slider 2061, a bearing 120, a connecting rod 130 and a bayonet sleeve 140. The bearing 120 is mounted on the slider 110; one end of the connecting rod 130 is connected with the transmission rod 605 or 6307 of the operation execution assembly 100, and the other end is provided with an annular slot in the circumferential direction. At least part of an inner wall face of the bayonet sleeve 140 is connected with the annular slot in a clamping manner, and the outer wall face of the bayonet sleeve 140 is fixedly connected with the inner wall face of the bearing 120.

The bayonet structure of the needle holder of the present invention brings about the following effects: 1. when the nut slider 2061 reciprocates linearly, the nut slider 2061 actuates the bearing 120 mounted thereon, the bayonet sleeve 140 and the connecting rod 130 do the same linear motion, achieving control of the opening and closing of the needle holder 640; and 2. when the transmission rod 605 rotates, the bearing 120 may allow the bayonet sleeve to achieve a spin motion, thereby reducing friction.

In one embodiment, the bayonet sleeve 140 includes two semicircular sleeves, and the two semicircular sleeves are spliced into the bayonet sleeve 140. In order to facilitate the clamping of the bayonet sleeve 140 into the annular slot of the connecting rod, the bayonet sleeve 140 is designed as two semicircles, and then pieced together to form the bayonet sleeve 140. It is worth noting that, a case that the bayonet sleeve 140 is spliced with multiple arc-shaped sleeves for ease of mounting is also within the protection scope of the present invention.

In one embodiment, the inner wall of the first end of the bayonet sleeve 140 forms an annular protrusion, and the annular protrusion is clamped into the annular slot. In an embodiment, the bayonet structure further includes a fixing sleeve 150, the second end of the bayonet sleeve 140 extends out of the bearing 120, and the outer wall face of the second end of the bayonet sleeve 140 is provided with external threads, so as to be connected with the fixing sleeve 150 by means of the thread, to realize the splicing of the two semicircular sleeves. That is, the fixing sleeve 150 is provided with internal threads, and the fixing sleeve 150 is in threaded and cooperative connection with the bayonet sleeve 140. After the annular protrusion of the bayonet sleeve 140 spliced by the two semicircular sleeves is clamped into the annular slot, the two semicircular sleeves need to be fixed to prevent the two semicircular sleeves from falling off. Therefore, the fixing sleeve 150 may implement fixing of the spliced bayonet sleeve 140, and then the fixed bayonet sleeve 140 is mounted on the bearing 120.

In one embodiment, one end of the fixing sleeve 150 abuts against the first side end face of the bearing 120 away from the connecting rod 130, so as to prevent the bearing 120 from falling off in one direction. The bearing 120 is configured with a baffle 160, and the baffle 160 abuts against a second side end face of the bearing 120 near the connecting rod 130, and the baffle 160 is fixed on the nut slider 2061; the bearing 120 is limited through the baffle 160 to prevent the bearing 120 from falling off from the other direction. The specific mode is as follows: the fixing sleeve 150 abuts against a small ring of the bearing 120, and the baffle 160 abuts against a large ring of the bearing 120 in the other direction, that is, two sides of the bearing 120 are limited by the fixing sleeve 150 and the baffle 160 respectively, thereby effectively preventing the bearing 120 from falling off.

In one embodiment, an inner hole of the bayonet sleeve 140 is of a stepped shape; the bayonet sleeve 140 includes a first stepped hole 1401 located at a first end of the bayonet sleeve 140 and a second stepped hole 1403 located at a second end of the bayonet sleeve 140. A diameter of the second stepped hole 1403 is larger than the diameter of the first stepped hole 1401; the first stepped hole 1401 is formed by the annular protrusions, and the annular slot is clamped and connected with the annular protrusion. The cross-sectional area of the second stepped hole 1403 of the bayonet sleeve is equal to or larger than the cross-sectional area of the connecting shaft 130, and a portion of the bayonet sleeve 140 corresponding to the second stepped hole 1403 extends out of the bearing 120. An inner surface of the bayonet sleeve 140 at the first stepped hole 1401 contacts and cooperates with the inner surface of the connecting rod 130 at the annular slot, so that the portion of the bayonet sleeve 140 is clamped into the annular slot. When the nut slider 2061 reciprocates linearly, the nut slider 2061 actuates the bearing 120 to move, and the bearing 120 actuates the bayonet sleeve 140 to move. Since the portion of the bayonet sleeve 140 is clamped into the annular slot, that is, the bayonet sleeve 140 actuates the connecting shaft 130 to move, and the connecting shaft 130 drives the needle holder 640, achieving the control of the opening and closing of the needle holder 640.

In one embodiment, the connecting rod 130 and the transmission rod 605 are detachably connected through a threaded cooperation, which facilitates the replacement of the transmission rod 605. Please note that detachable connecting means that the connection mode of the connecting rod 130 and the transmission rod 605 is detachable, including a threaded connection, a screw connection or other detachable connection modes, which should be within the protection scope of the present invention.

In one embodiment, the nut slider 2061 is provided with a mounting hole that cooperates with the bearing 120, and the outer wall face of the bearing 120 contacts and cooperates with the inner wall face of the nut slider 2061 at the mounting hole. The mounting mode of the bearing 120 is already a mature technology in the art, and will not be described in detail here.

Figure 25:
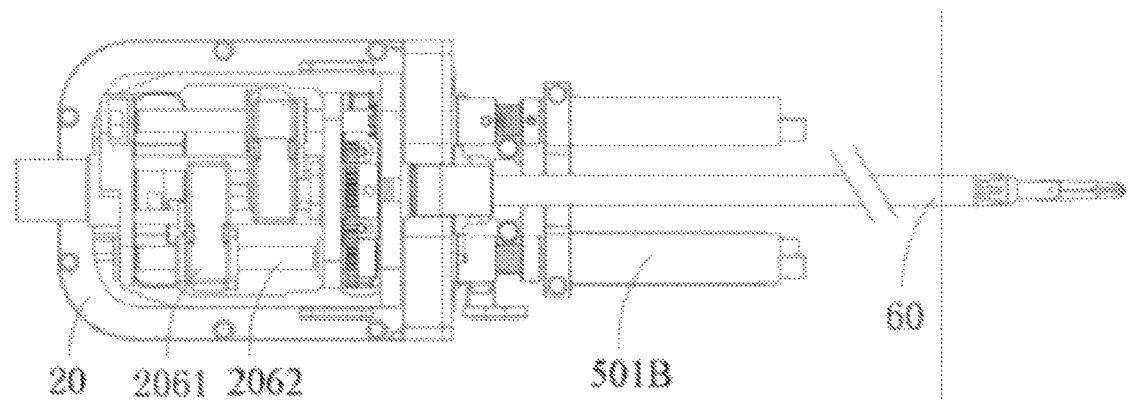
FIG. 25 is a structural schematic view of a control assembly of a needle holder.

In the embodiment shown in FIGS. 25-27, a control assembly includes the bayonet structure described above, and the control assembly further includes a driving means connected with the nut slider 2061 to enable the nut slider 2061 to move linearly. The driving means includes a screw 2062 and a motor 501B, the screw 2062 is in threaded and cooperative connection with the nut slider 2061, and the motor 50 is connected with the screw 2062 by a coupling, wherein the motor 501B drives the screw 2062 to rotate to enable the nut slider 2061 to move linearly; and the control assembly further includes an instrument seat 20, and the screw 2062 is rotatably mounted on the instrument seat 20. The instrument seat 110 is provided with a guide position-limiting rod (not marked in the figure) that limits the rotation of the slider. Specifically, the nut slider 2061 is provided with a guide hole, and the guide position-limiting rod passes through the guide hole and contacts and cooperates with the nut slider 2061. When the screw 2061 is rotated by means of the thread, since the nut slider 2061 is cooperated with the screw 2061 by means of the thread and is limited by the guide position-limiting rod, the nut slider 2061 moves along the guide position-limiting rod (the screw 2062). The motor 50 drives the screw 2061 to rotate forward and backward. When the screw 2061 rotates, the nut slider 2061 is actuated to reciprocate linearly; the nut slider 2061 actuates the bearing 120 to move, and the bearing 120 actuates the bayonet sleeve 140 to move. Since a portion of the bayonet sleeve 140 is clamped into the annular slot, that is, the bayonet sleeve 140 actuates the connecting shaft 130 to move, and the connecting shaft 130 drives the transmission rod, achieving the control the opening and closing of the operation execution assembly.

VI. Operation Execution Assembly 100

Figure 29:
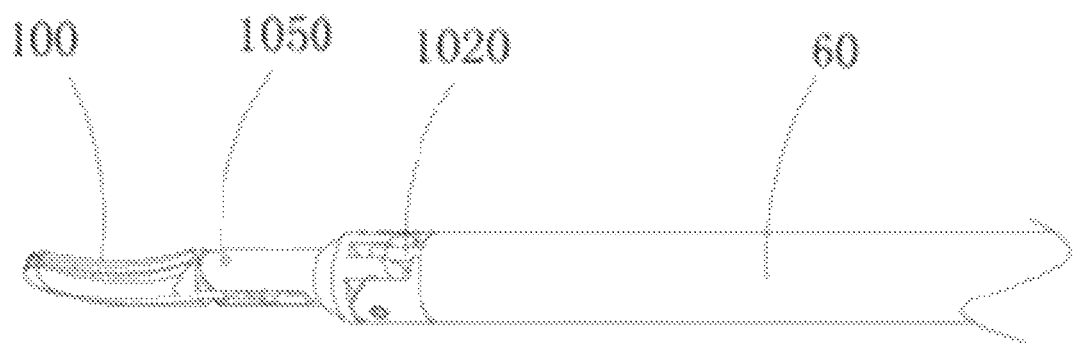
FIG. 29 is a structural schematic view of a surgical instrument.

The embodiment shown in FIG. 29 provides a surgical instrument, including an operation execution assembly 100, an opening-closing control assembly 1050, a spin control assembly 1040 and a deflection control assembly 1020; the opening-closing control assembly 1050 is connected with the execution assembly 100. The spin control assembly 1040 and the opening-closing control assembly 1050 are hingedly provided; the deflection control assembly 1020 includes a first transmission member connected with the opening-closing control assembly 1050, wherein the first transmission member is pushed and pulled to move, so that the opening-closing control assembly 1050 actuates the execution assembly 100 to deflect around a hinge point.

Figure 30:
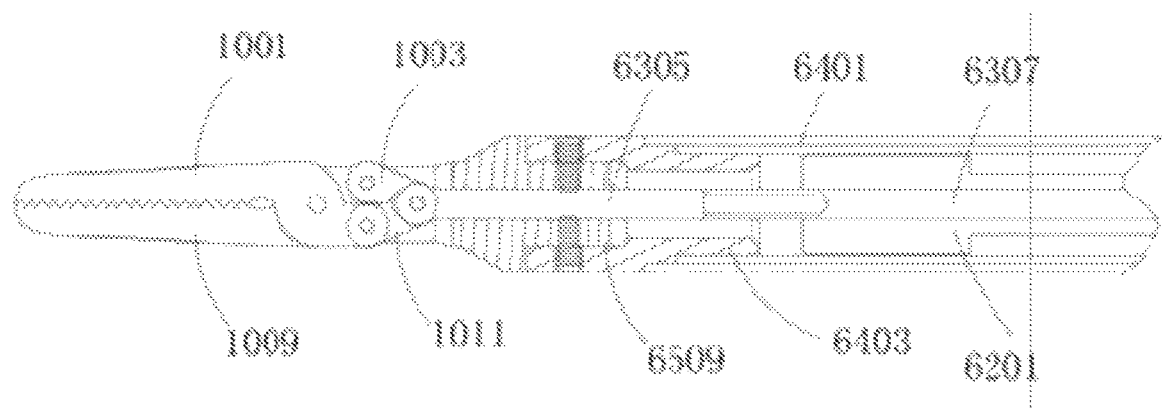
FIG. 30 is a structural schematic view of an opening-closing control assembly of a surgical instrument.

In the embodiment shown in FIG. 30, the first transmission member includes a first transmission rod 6031 and a movable rod 6033; one end of the movable rod 6033 is rotatably connected with the first transmission rod 6031, and the other end is rotatably connected with the opening-closing control assembly 1050, and the manner where the movable rod 6033 is connected with each of the first transmission rod 6031 and the opening-closing control assembly 1050 includes but not limited to a pin connection. When the first transmission rod 6031 reciprocates, the movable rod 6033 pushes the opening-closing control assembly 1050 to bend or straighten at a hinge, and the opening-closing control assembly 1050 actuates the execution assembly 100 to bend or straighten, thereby achieving the bending and straightening of the execution assembly 100 at a wrist, such that the execution assembly 100 implements a wrist joint action similar to that of a human hand, achieving the effect of synchronizing the manipulation of the surgical instrument and the human hand, and reducing the difficulty of the manipulation of the surgical instrument.

In the embodiment shown in FIG. 2, the spin control assembly 1040 includes a second transmission member, and the opening-closing control assembly 1050 is hingedly provided at the second transmission member; the second transmission member includes a second transmission rod 6401 and a connecting sleeve 6403. The second transmission rod 6401 is fixedly connected with the connecting sleeve 6403, the opening-closing control assembly 1050 is hinged with the connecting sleeve 6403 by a pin; the spin control assembly 1040 is driven to rotate, the spin control assembly 1040 actuates the opening-closing control assembly 1050 to rotate, and the opening-closing control assembly 1050 actuates the execution assembly 100 to rotate, so that the operation execution assembly 100 implements a spin action, ensuring the smooth progress of the operation, and also improving the versatility of operation instruments of the operation robot.

In the embodiment shown in FIG. 30, the execution assembly 100 includes an operation scissor; the execution assembly 100 includes a first plier body 1001 and a second plier body 1009, the first plier body 1001 and the second plier body 1009 are provided in an intersecting manner, and the first plier body 1001 is rotatably connected with the second plier body 1009 by a pin at the intersecting area therebetween. By providing the first plier body 1001 and the second plier body 1009 in a rotating and intersecting manner, opening and closing of the execution assembly 100 may be implemented.

In the embodiment shown in FIG. 30, the opening-closing control assembly 1050 includes a transition member, the transition member includes a first transition rod 1011 and a second transition rod 1003. One end of the first transition rod 1011 is rotatably connected with the first plier body 1003, and one end of the second transition rod 1003 is rotatably connected with the second plier body 1009.

In the embodiment shown in FIG. 30, the opening-closing control assembly 1050 further includes a third transmission member; the third transmission member includes a third transmission rod 6307 and a connecting rod 6305; one end of the connecting rod 6305 is connected with the third transmission rod 6307, the other end of each of the first transition rod 1011 and the second transition rod 1003 is rotatably connected with the other end of the connecting rod 6305, wherein the execution assembly 100 is opened and closed following the reciprocation of the third transmission rod 6307. The specific mode is as follows. First, the first plier body 1001 and second plier body 1009 are provided in an intersecting manner; then, a pin is inserted at the intersecting area of the first plier body 1001 and second plier body 1009, so that the first plier body 1001 and second plier body 1009 is rotatably connected with the pin; then, one end of each of the first transition rod 6305 and the second transition rod 1003 is rotatably connected with the connecting rod 6305; then, the other end of the first transition rod 1011 is rotatably connected with the first plier body 1001, and at the same time, the other end of the second transition rod 1003 is rotatably connected with the second plier body 1009, so that the first transition rod 1011, the second transition rod 1003, the first plier body 1001 and the second plier body 1009 form a quadrangle; thereafter, when the third transmission rod 6307 actuates the connecting rod 6305 to reciprocate, the first transition rod 1011 and the second transition rod 1003 are actuated to rotate, so that the first transition rod 1011 and the second transition rod 1003 push the first plier body 1001 and the second plier body 1009 to open or close, thereby actuating the surgical instrument 100 to open or close, achieving the driving of the surgical instrument 100.

In one embodiment, the connecting rod 6305 is a flexible connecting rod, which may bear an axial force, and thus the connecting rod 6305 does not bend when bearing an axial force, and when the connecting rod 6305 bends when bearing a radial force. Therefore, the connecting rod 6305 may implement reciprocation along the axial direction. When the opening-closing control assembly 1050 and the execution assembly 100 need to perform a wrist joint swing motion, the connecting rod 6305 may be bent due to a radial force.

In the embodiment shown in FIG. 30, the opening-closing control assembly 1050 includes a mounting seat 10509, the mounting seat 10509 of the opening-closing control assembly 1050 is hinged with a connecting sleeve 6403 by a pin. Two ends of said movable rod 6033 are rotatably connected with the first transmission rod 6031 and the mounting seat 10509 of the opening-closing control assembly respectively, and the specific mode includes but not limited to a pin connection.

Figure 31:
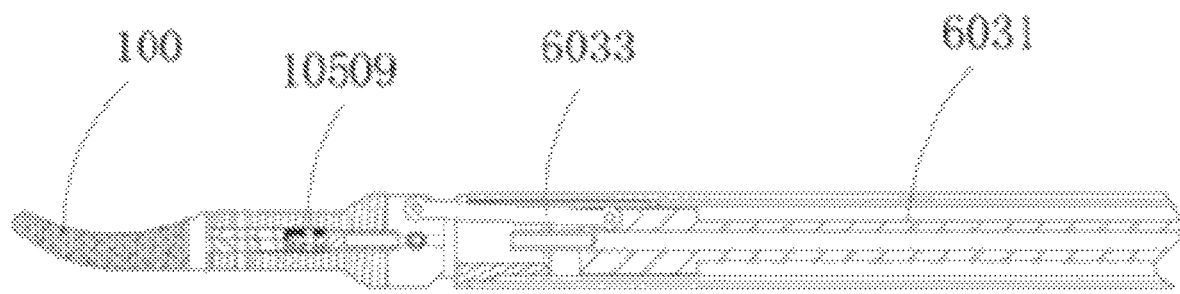
FIG. 31 is a structural schematic view of a deflection control assembly of a surgical instrument.
Figure 32:
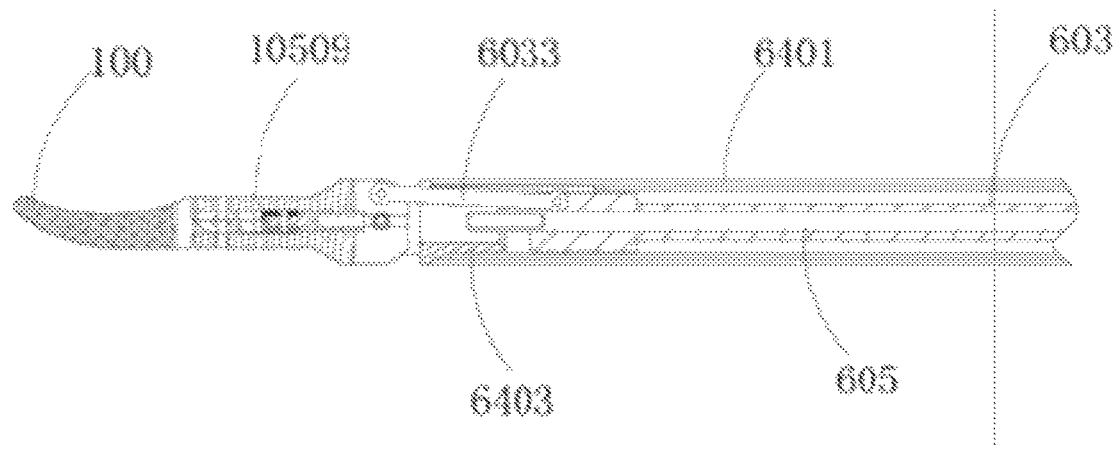
FIG. 32 is a structural schematic view of a spin control assembly of a surgical instrument.

In the embodiment shown in FIGS. 31 and 32, the second transmission rod 6401 and the first transmission rod 603 are both of a hollow structure, and the first transmission rod 603 is provided in the second transmission rod 6401, and the third transmission rod 605 is provided in the first transmission rod 603. The surgical instrument has an overall simple structure and may effectively reduce the volume of the surgical instrument of the surgical robot, so that the operation execution assembly can quickly and accurately complete the instructions issued by the doctor in a limited space.

One embodiment is provided with a surgical robot including the surgical instrument as described above. The surgical instrument has been described in detail in the above, and will not be repeated here.

In this description, the term "a plurality of" refers to two or more than two. Unless otherwise clearly defined, orientation or positional relations indicated by terms such as "upper" and "lower" are based on the orientation or positional relations as shown in the FIG.s, only for facilitating description of the present utility model and simplifying the description, rather than indicating or implying that the referred devices or elements must be in a particular orientation or constructed or operated in the particular orientation, and therefore they should not be construed as limiting the present utility model. The terms "connected", "mounted", "fixed", etc. should be understood in a broad sense. For example, "connected" may be a fixed connection, a detachable connection, or an integral connection; a direct connection, or an indirect connection through an intermediate medium. For an ordinary skilled in the art, the specific meaning of the above terms in the present utility model may be understood according to specific circumstances.

In this description, the descriptions of the terms "an embodiment", "some embodiments", "specific embodiments", etc. intend to mean that the specific features, structures, materials, or features described in combination with the embodiments or examples are included in at least one embodiment or example of the utility model of the present utility model. In the present invention, the schematic expressions of the above terms do not necessarily refer to the same embodiment or example. Moreover, the described specific features, structures, materials or characteristics may be combined in any one or more embodiments or examples in a suitable manner.

Although the disclosed embodiments of the present invention are as described above, the content described is only used to facilitate the understanding of the present invention, and is not intended to limit the present invention. Any person skilled in the technical field of the present invention may make any modifications and changes in the form and details of implementation without departing from the spirit and scope of the present invention. However, the protection scope of the present invention shall be determined based on the scope defined by the appended claims.

What is claimed:

1. A component mounting frame for use with a robotic surgical system, comprising:
   (a) an instrument seat, wherein the instrument seat supports a transmission, wherein the instrument seat includes an upper portion and a lower portion, and wherein the lower portion of the instrument seat includes a slot component therein, and wherein the slot component includes a plurality of communicating-interface devices;
   (b) a sterile isolation seat, wherein the sterile isolation seat supports a sterile isolation membrane, wherein the sterile isolation seat includes an upper portion and a lower portion, wherein the upper portion of the instrument seat includes a block component thereon that includes a plurality of communicating-interfacing devices and that detachably connects to the slot component on the lower portion of the instrument seat and forms a communication interface therewith, and wherein the lower portion of the instrument seat includes a slot component therein, and wherein the slot component includes a plurality of communicating-interface devices; and
   (c) a motor mounting seat, wherein the motor mounting seat supports a driver, wherein the motor mounting seat includes an upper portion and a lower portion, and wherein the upper portion of the motor mounting seat includes a block component thereon that includes a plurality of communicating-interfacing devices and that detachably connects to the slot component on the lower portion of the sterile isolation seat and forms a communication interface therewith;
   (d) a control assembly, wherein a first end of the control assembly is connected to the transmission, and wherein the transmission includes one or more actuator assemblies connected to one or more driving assemblies for providing motion to the control assembly;
   (e) an execution assembly, wherein the execution assembly includes first and second plier bodies, and wherein the execution assembly is connected to a second end of the control assembly in a hinged manner for permitting the control assembly to open the plier bodies, close the plier bodies, spin the execution assembly axially, and deflect the execution assembly around the hinge;
   (f) a bayonet structure connected to the control assembly within the transmission for providing opening, closing, and rotation to the execution assembly, wherein the bayonet structure includes:
      (a) a slider;
      (b) a bearing mounted on the slider;
      (c) a connecting rod, wherein a first end of the connecting rod is connected to the control assembly, and wherein a second end of the connecting rod includes a circumferentially-oriented annular slot; and
      (d) a bayonet sleeve, wherein one portion of the bayonet sleeve is clamped to the annular slot, and wherein one portion of the bayonet sleeve is connected in a fixed manner to the bearing.

2. The component mounting frame of claim 1, further comprising:
   (a) a first coupling on the instrument seat;
   (b) a second coupling on the sterile isolation seat, wherein the second coupling is connected to the first coupling; and
   (c) a third coupling on the motor mounting seat, where in the third coupling is connected to the second coupling,
   (d) wherein the first coupling, second coupling, and third coupling are coaxially aligned with one another, and
   (e) wherein the driver provides power to the transmission through the coaxially aligned first, second, and third couplings.

3. The component mounting frame of claim 1, further comprising a deflection control assembly and an opening-closing control assembly disposed between the control assembly and the execution assembly, wherein the deflection control assembly includes one or more transmission members connected to the opening-closing control assembly, and wherein the transmission members are adapted to be pushed and pulled in a manner that causes the opening-closing control assembly to both actuate the execution assembly and allow the execution assembly to deflect around a hinge point.

4. The component mounting frame of claim 1, wherein the plier bodies include intersecting, hingeably connected first and second plier bodies.

5. The component mounting frame of claim 1, wherein the execution assembly includes an operation scissors.

6. The component mounting frame of claim 1, wherein the instrument seat, sterile isolation seat, and motor mounting seat are coaxially aligned with one another.

7. The component mounting frame of claim 1, wherein the instrument seat, sterile isolation seat, motor mounting seat, control assembly, and execution assembly are coaxially aligned with one another.

8. A component mounting frame for use with a robotic surgical system, comprising:
   (a) an instrument seat, wherein the instrument seat supports a transmission, wherein the instrument seat includes an upper portion and a lower portion, and wherein the lower portion of the instrument seat includes a slot component therein, and wherein the slot component includes a plurality of communicating-interface devices;
   (b) a sterile isolation seat, wherein the sterile isolation seat supports a sterile isolation membrane, wherein the sterile isolation seat includes an upper portion and a lower portion, wherein the upper portion of the instrument seat includes a block component thereon that includes a plurality of communicating-interfacing devices and that detachably connects to the slot component on the lower portion of the instrument seat and forms a communication interface therewith, and wherein the lower portion of the instrument seat includes a slot component therein, and wherein the slot component includes a plurality of communicating-interface devices;
   (c) a motor mounting seat, wherein the motor mounting seat supports a driver, wherein the motor mounting seat includes an upper portion and a lower portion, and wherein the upper portion of the motor mounting seat includes a block component thereon that includes a plurality of communicating-interfacing devices and that detachably connects to the slot component on the lower portion of the sterile isolation seat and forms a communication interface therewith;

(d) a control assembly, wherein a first end of the control assembly is connected to the transmission, and wherein the transmission includes one or more actuator assemblies connected to one or more driving assemblies for providing motion to the control assembly; and (e) an execution assembly, wherein the execution assembly includes first and second plier bodies, and wherein the execution assembly is connected to a second end of the control assembly in a hinged manner for permitting the control assembly to open the plier bodies, close the plier bodies, spin the execution assembly axially, and deflect the execution assembly around the hinge, (f) wherein the instrument seat, sterile isolation seat, motor mounting seat, control assembly, and execution assembly are coaxially aligned with one another;

(g) a bayonet structure connected to the control assembly within the transmission for providing opening, closing, and rotation to the execution assembly, wherein the bayonet structure includes:
  (a) a slider;
  (b) a bearing mounted on the slider;
  (c) a connecting rod, wherein a first end of the connecting rod is connected to the control assembly, and wherein a second end of the connecting rod includes a circumferentially-oriented annular slot; and
  (d) a bayonet sleeve, wherein one portion of the bayonet sleeve is clamped to the annular slot, and wherein one portion of the bayonet sleeve is connected in a fixed manner to the bearing.

9. The component mounting frame of claim 8, further comprising:
  (a) a first coupling on the instrument seat;
  (b) a second coupling on the sterile isolation seat, wherein the second coupling is connected to the first coupling; and
  (c) a third coupling on the motor mounting seat, where in the third coupling is connected to the second coupling,
  (d) wherein the first coupling, second coupling, and third coupling are coaxially aligned with one another, and
  (e) wherein the driver provides power to the transmission through the coaxially aligned first, second, and third couplings.

10. The component mounting frame of claim 8, further comprising a deflection control assembly and an opening-closing control assembly disposed between the control assembly and the execution assembly, wherein the deflection control assembly includes one or more transmission members connected to the opening-closing control assembly, and wherein the transmission members are adapted to be pushed and pulled in a manner that causes the opening-closing control assembly to both actuate the execution assembly and allow the execution assembly to deflect around a hinge point.

11. The component mounting frame of claim 8, wherein the plier bodies include intersecting, hingeably connected first and second plier bodies.

12. The component mounting frame of claim 8, wherein the execution assembly includes an operation scissors.

13. A component mounting frame for use with a robotic surgical system, comprising:

(a) an instrument seat, wherein the instrument seat supports a transmission, wherein the instrument seat includes an upper portion and a lower portion, and wherein the lower portion of the instrument seat includes a slot component therein, and wherein the slot component includes a plurality of communicating-interface devices;

(b) a sterile isolation seat, wherein the sterile isolation seat supports a sterile isolation membrane, wherein the sterile isolation seat includes an upper portion and a lower portion, wherein the upper portion of the instrument seat includes a block component thereon that includes a plurality of communicating-interfacing devices and that detachably connects to the slot component on the lower portion of the instrument seat and forms a communication interface therewith, and wherein the lower portion of the instrument seat includes a slot component therein, and wherein the slot component includes a plurality of communicating-interface devices;

(c) a motor mounting seat, wherein the motor mounting seat supports a driver, wherein the motor mounting seat includes an upper portion and a lower portion, and wherein the upper portion of the motor mounting seat includes a block component thereon that includes a plurality of communicating-interfacing devices and that detachably connects to the slot component on the lower portion of the sterile isolation seat and forms a communication interface therewith;

(d) a first coupling on the instrument seat;

(e) a second coupling on the sterile isolation seat, wherein the second coupling is connected to the first coupling;

(f) a third coupling on the motor mounting seat, where in the third coupling is connected to the second coupling;

(g) a control assembly, wherein a first end of the control assembly is connected to the transmission, and wherein the transmission includes one or more actuator assemblies connected to one or more driving assemblies for providing motion to the control assembly;

(h) an execution assembly, wherein the execution assembly includes first and second plier bodies, and wherein the execution assembly is connected to a second end of the control assembly in a hinged manner for permitting the control assembly to open the plier bodies, close the plier bodies, spin the execution assembly axially, and deflect the execution assembly around the hinge;

(i) a bayonet structure connected to the control assembly within the transmission for providing opening, closing, and rotation to the execution assembly, wherein the bayonet structure includes:
  (a) a slider;
  (b) a bearing mounted on the slider;
  (c) a connecting rod, wherein a first end of the connecting rod is connected to the control assembly, and wherein a second end of the connecting rod includes a circumferentially-oriented annular slot; and
  (d) a bayonet sleeve, wherein one portion of the bayonet sleeve is clamped to the annular slot, and wherein one portion of the bayonet sleeve is connected in a fixed manner to the bearing, (g) wherein the first coupling, second coupling, and third coupling are coaxially aligned with one another, (h) wherein the driver provides power to the transmission through the coaxially aligned first, second, and third couplings, and (i) wherein the instrument seat, sterile isolation seat, and motor mounting seat are coaxially aligned with one another.

14. The component mounting frame of claim 13, further comprising a deflection control assembly and an opening-closing control assembly disposed between the control assembly and the execution assembly, wherein the deflection control assembly includes one or more transmission members connected to the opening-closing control assembly, and wherein the transmission members are adapted to be pushed and pulled in a manner that causes the opening-closing control assembly to both actuate the execution assembly and allow the execution assembly to deflect around a hinge point.

15. The component mounting frame of claim 13, wherein control assembly and execution assembly are coaxially aligned with one another, and wherein the control assembly and execution assembly are coaxially aligned with the instrument seat, sterile isolation seat, and motor mounting seat.

* * * * *